(12) United States Patent
Sumida et al.

(10) Patent No.: US 10,589,076 B2
(45) Date of Patent: Mar. 17, 2020

(54) OPERATIONAL INSTRUMENT FOR FLUID INJECTOR USING MULTI-MICRONEEDLE DEVICE

(71) Applicant: TOPPAN PRINTING CO., LTD., Taito-ku (JP)

(72) Inventors: Tomoya Sumida, Taito-ku (JP); Yumiko Ikeda, Taito-ku (JP); Masaki Kono, Taito-ku (JP)

(73) Assignee: TOPPAN PRINTING CO., LTD., Tokyo (JP)

( * ) Notice: Subject to any disclaimer, the term of this patent is extended or adjusted under 35 U.S.C. 154(b) by 771 days.

(21) Appl. No.: 14/584,213

(22) Filed: Dec. 29, 2014

(65) Prior Publication Data
US 2015/0112269 A1    Apr. 23, 2015

Related U.S. Application Data

(63) Continuation of application No. PCT/JP2013/066979, filed on Jun. 20, 2013.

(30) Foreign Application Priority Data

Jun. 26, 2012  (JP) ................................ 2012-142936
Jul. 25, 2012  (JP) ................................ 2012-164702

(51) Int. Cl.
*A61M 37/00*   (2006.01)
*A61M 5/42*    (2006.01)
*A61M 5/142*   (2006.01)

(52) U.S. Cl.
CPC ........ *A61M 37/0015* (2013.01); *A61M 5/425* (2013.01); *A61M 2005/14252* (2013.01);
(Continued)

(58) Field of Classification Search
CPC ...... A61M 37/0015; A61M 2037/0023; A61M 2037/003; A61M 2037/0061;
(Continued)

(56) References Cited

U.S. PATENT DOCUMENTS 5,415,645 A * 5/1995 Friend .................. A61M 5/326
                                                        604/110
5,540,561 A * 7/1996 Johnson ................ A61M 5/142
                                                       128/DIG. 12
(Continued)

FOREIGN PATENT DOCUMENTS

EP  2 460 553 A1   6/2012
JP  2002-355317    12/2002
JP  2010-532219    10/2010

OTHER PUBLICATIONS

Extended European Search Report dated Jan. 20, 2016 in Patent Application No. 13808907.3.
(Continued)

*Primary Examiner* — Nilay J Shah
(74) *Attorney, Agent, or Firm* — Oblon, McClelland, Maier & Neustadt, L.L.P.

(57) ABSTRACT

An operation tool for a fluid injector includes an outer cylinder having a housing extending from a first open end to a second open end, and a selective transfer mechanism provided on the outer cylinder. The selective transfer mechanism moves the fluid injector from an initial position to a first protrusion position and then to a second protrusion position in the housing of the outer cylinder. When the fluid injector is at the initial position, the multi-microneedle device has microneedles retracted from the first open end and positioned inside the housing, when the fluid injector is at the first protrusion position, the microneedles are pro-
(Continued)

truded out to a first distance from the first open end, and when the fluid injector is at the second protrusion position, the microneedles are protruded out to a second distance from the first open end. The second distance is shorter than the first distance.

20 Claims, 9 Drawing Sheets

(52) U.S. Cl.
CPC ............... *A61M 2037/003* (2013.01); *A61M 2037/0023* (2013.01); *A61M 2037/0061* (2013.01)

(58) Field of Classification Search
CPC ...... A61M 2005/14252; A61M 5/3287; A61M 5/31581; A61B 17/205; A61B 5/150175; A61B 5/150183; A61B 5/15019; A61B 5/150198

See application file for complete search history.

(56) References Cited

U.S. PATENT DOCUMENTS

| | | | |
|---|---|---|---|
| 6,599,272 B1* | 7/2003 | Hjertman | A61M 5/315 604/197 |
| 2002/0161335 A1 | 10/2002 | Metzner et al. | |
| 2005/0165358 A1* | 7/2005 | Yeshurun | A61M 37/0015 604/173 |
| 2008/0027384 A1 | 1/2008 | Wang et al. | |
| 2008/0058732 A1* | 3/2008 | Harris | A61M 5/20 604/235 |
| 2008/0171996 A1* | 7/2008 | Lafferty | A61M 5/001 604/187 |
| 2008/0200863 A1 | 8/2008 | Chomas et al. | |
| 2009/0312707 A1* | 12/2009 | Bishop | A61M 5/24 604/135 |
| 2014/0296825 A1 | 10/2014 | Lemaire et al. | |

OTHER PUBLICATIONS

U.S. Appl. No. 14/605,436, filed Jan. 26, 2015, Sumida, et al.
U.S. Appl. No. 14/689,541, filed Apr. 17, 2015, Sumida, et al.
International Search Report dated Aug. 6, 2013, in International Application No. PCT/JP2013/066979.

* cited by examiner

OPERATIONAL INSTRUMENT FOR FLUID INJECTOR USING MULTI-MICRONEEDLE DEVICE

CROSS-REFERENCE TO RELATED APPLICATIONS

The present application is a continuation of International Application No. PCT/JP2013/066979, filed Jun. 20, 2013, which is based upon and claims the benefits of priority to Japanese Application No. 2012-142936, filed Jun. 26, 2012 and Japanese Application No 2012-164702, filed Jul. 25, 2012. The entire contents of all of the above applications are incorporated herein by reference.

BACKGROUND OF THE INVENTION

Technical Field

The present invention relates to an operational instrument for a fluid injector using a multi-microneedle device.

Background Art

A fluid injector using a multi-microneedle device is known in a medical field. Such a fluid injector in a medical field is known as a syringe.

The fluid injector includes a fluid holding cylinder (a syringe barrel in a syringe) having a fluid holding space, a fluid outflow port, and a fluid holding space inlet opening. The fluid holding space is long and thin, and capable of holding a given amount of a fluid (for example, a medicinal solution in a medical field). The fluid outflow port is provided at one end of a longitudinal direction of the fluid holding space, and the fluid of the fluid holding space can be discharged therefrom. The fluid holding space inlet opening is provided at the other end of the longitudinal direction of the fluid holding space. The fluid injector further has a piston member inserted in the fluid holding space of the fluid holding cylinder from the fluid holding space inlet opening so as to enable it to slide along the above longitudinal axis.

It is considered that the multi-microneedle device in a medical field is attached to an outflow port of a syringe barrel of a conventional syringe in place of one syringe needle well known in a medical field, and used for intradermal injection. The multi-microneedle device includes a main body where an outflow port attachment port and a fluid holding space are formed. The outflow port attachment port is detachably attached to the fluid outflow port of the fluid (a medicinal solution in a medical field) of the syringe barrel. The fluid holding space temporarily holds the fluid which has been subjected to pressure of the piston member of the syringe barrel to be discharged from the fluid outflow port to the outflow port attachment port. The multi-microneedle device has a plurality of microneedles disposed on a plane positioned on the opposite side to the outflow port attachment port across the fluid holding space.

The above plane of the main body functions as a skin contact surface. The microneedles have respective fine fluid injection passages extending between base ends on the above plane and head ends away from the above plane. Lengths between the above respective base ends and the above respective head ends of the microneedles (i.e., respective heights of the microneedles) are set within a range of thicknesses of skin tissues of a living thing (for example, all human-beings) having the skin tissue as a use target.

SUMMARY OF INVENTION

According to one aspect of the present invention, an operation tool for a fluid injector having a multi-microneedle device includes: an outer cylinder having a first open end, a second open end, and a housing extending from the first open end to the second open end, the housing being formed such that a fluid injector having a multi-microneedle device is movable in the housing along a longitudinal axis of the fluid injector; and a selective transfer mechanism which is provided on the outer cylinder and moves the fluid injector from an initial position to a first protrusion position and then to a second protrusion position in the housing of the outer cylinder. The selective transfer mechanism is structured such that, when the fluid injector is at the initial position, the multi-microneedle device has microneedles retracted from the first open end of the outer cylinder and positioned inside the housing, when the fluid injector is at the first protrusion position, the microneedles are protruded out to a first distance from the first open end, and when the fluid injector is at the second protrusion position to discharge fluid through the microneedles of the multi-microneedle device, the microneedles are protruded out to a second distance from the first open end. The second distance is shorter than the first distance.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1A:
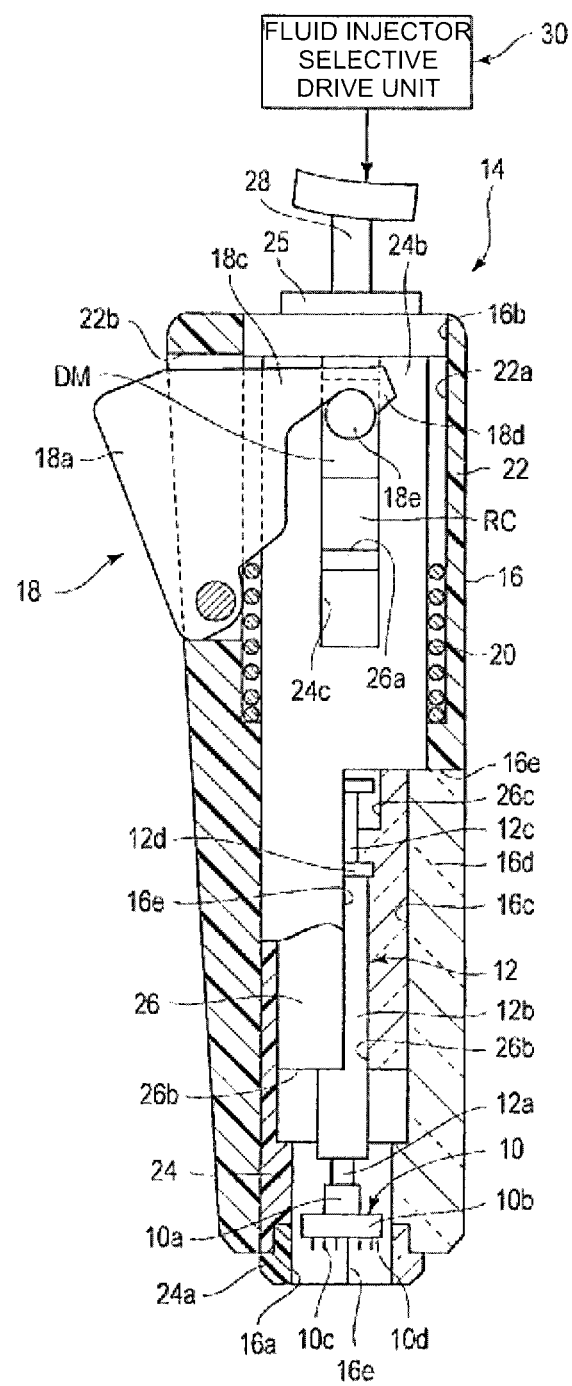
FIG. 1A is a schematic longitudinal sectional view of an operational instrument, for a fluid injector using a multi-microneedle device, according to a first embodiment.

The embodiments will now be described with reference to the accompanying drawings, wherein like reference numerals designate corresponding or identical elements throughout the various drawings.

First Embodiment

Figure 1B:
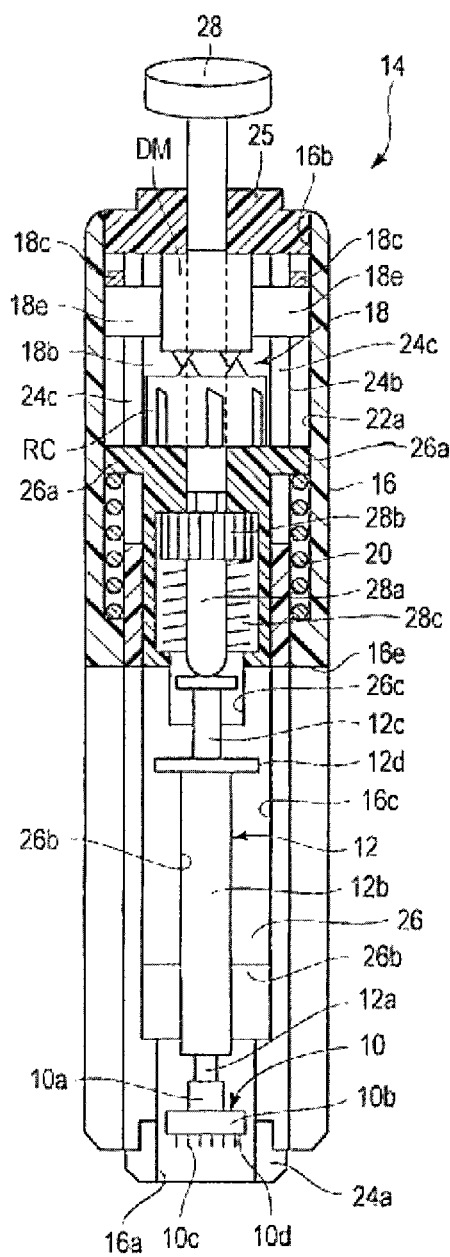
FIG. 1B is another schematic longitudinal sectional view in a direction intersecting the longitudinal section of FIG. 1A at a right angle, of the operational instrument according to the first embodiment. Here, a detachable and attachable part of a periphery wall of an outer cylinder of the operational instrument, and, a detachable and attachable part of a fluid injector holding detachable and attachable body to hold a fluid injector detachably in a fluid injector housing space corresponding to a part of the periphery wall of the outer cylinder is detached.

With reference to FIGS. 1A and 1B, at first is schematically described a structure of an operational instrument 14, for a fluid injector 12 using a multi-microneedle 10, according to a first embodiment.

It is studied to use, for example, as a syringe in a medical field, the fluid injector 12 using the multi-microneedle device 10 operated by the operational instrument 14 according to the first embodiment.

The fluid injector 12 has a fluid holding cylinder 12b (a syringe barrel in a syringe). The fluid holding cylinder 12b has a long and thin fluid holding space, a fluid outflow port 12a, and a fluid holding space inlet. The fluid holding space is capable of holding given fluid (for example, medicinal solution in a medical field). The fluid outflow port 12a is disposed at one end in longitudinal directions of the fluid holding space, and the fluid of the fluid holding space outflows from the fluid outflow port 12a. The fluid holding space inlet is disposed at the other one end in the longitudinal directions of the fluid holding space. The fluid injector 12 further has a piston member 12c set in the fluid holding space of the fluid holding cylinder 12b from the fluid holding space inlet such as to slide along the longitudinal axis.

It is considered that the multi-microneedle device 10 in a medical field is attached to an outflow port of a syringe barrel of a conventional syringe in place of one syringe needle well known in the medical field, and used for intradermal injection.

The multi-microneedle device 10 includes a main body 10b having an outflow port attachment port 10a detachably attached to the fluid outflow port 12a of the fluid (medicinal solution in a medical field) of the fluid holding cylinder 12b (syringe barrel in a syringe) of the fluid injector 12. The main body 10b further forms a fluid holding space for temporarily holding fluid which has been subjected to pressure of a piston member 12c of the fluid injector 12 to be outflowed from the fluid outflow port 12a to the outflow port attachment port 10a. The multi-microneedle device 10 has a plurality of microneedles 10c disposed on a plane positioned on the opposite side to the outflow port attachment port 10a across the fluid holding space.

The multi-microneedle device 10 can be prepared by, for example, applying etching using a publicly known photolithography method on a silicon substrate. Moreover, by electroforming with the silicon multi-microneedle device as an original plate, a copy plate having a reversal shape is prepared. Thereby, a resin multi-microneedle device can also be prepared from the copy plate.

Regarding the multi-microneedle device, at least the plurality of microneedles 10c are preferred to be made of biocompatible materials, and the whole of the multi-microneedle device is further preferred to be made of biocompatible materials. The biocompatible materials include a metal including, for example, stainless steel, titanium, manganese or the like, a resin including, for example, medical silicone, polylactic acid, polyglycolic acid, polycarbonate or the like, or an inorganic material such as silicon.

The above described biocompatible materials can be shaped into at least the plurality of microneedles 10c of the multi-microneedle device or the whole of the multi-microneedle device by a publicly known forming technique such as injection forming, imprint, hot embossing, or casting.

The above plane of the main body 10b functions as a skin contact surface 10d. The microneedles have respective fine fluid injection passages extending between base ends on the above plane and head ends away from the above plane. Lengths between the above respective base ends and the above respective head ends of the microneedles 10c, that is, respective heights of the microneedles 10c are set within a range of thicknesses of skin tissues of a living thing (for example, all human beings) having the skin tissue as a use target, preferably within a range of thicknesses of the skin tissues having no nerves. Specifically, the height of the microneedle 10c is preferred to be set within a range of 100-2000 μm.

Each whole shape of the microneedles 10c may be a cone shape including a circular cone or a pyramid, or, a column or a prism having a circular conic or a pyramid tip. Formation of the respective fine fluid outflow passages of the microneedles 10c can be carried out by a publicly known fine hole making process using, for example, a micro drill, a laser light, or the like.

The microneedles 10c on the above plane of the main body 10b can be arranged in a lattice pattern, in a concentric pattern, at random or the like, depending on purposes of use.

The operational instrument 14 according to the first embodiment has an outer cylinder 16. The outer cylinder 16 has one opening end 16a, another opening end 16b, and a fluid injector housing space 16c extending between the one opening end 16a and the other opening end 16b. The fluid injector housing space 16c holds the fluid injector 12 using the multi-microneedle device 10 such that the fluid injector 12 can move along the longitudinal axis of the fluid injector 12.

The operational instrument 14 according to the first embodiment is provided in the outer cylinder 16, and further has a selective transfer mechanism 18 that serially moves the fluid injector 12 between an initial position, a first protrusion position and a second protrusion portion in the fluid injector housing space 16c of the outer cylinder 16.

The selective transfer mechanism 18 of the operational instrument 14 according to the first embodiment is configured to return the fluid injector 12 to the initial position after being at the second position in the fluid injector housing space 16c of the outer cylinder 16.

In the fluid injector 12 at the initial position, the skin contact surface 10d of the main body 10a of the multi-microneedle device 10 with the microneedles 10c, as shown in FIGS. 1A and 1B, is drawn into the fluid injector housing space 16c from the one opening end 16a of the outer cylinder 16.

In the fluid injector 12 at the first protrusion position, the skin contact surface 10d of the main body 10a of the multi-microneedle device 10 with the microneedles 10c is externally protruded out to a first distance away from the one opening end 16a of the outer cylinder 16.

In the fluid injector 12 at the second protrusion position, the skin contact surface 10d of the main body 10a of the multi-microneedle device 10 with the microneedles 10c is externally protruded out to a second distance away from the one opening end 16a of the outer cylinder 16, the second distance being shorter the above first distance.

In the operational instrument 14 according to the first embodiment, fluid flows out from the fluid injector 12 at the second protrusion position through the fluid injection passage of the microneedles 10c.

The selective transfer mechanism 18 of the operational instrument 14 according to the first embodiment has an operational member 18a and an operational member operation following mechanism 18b. The operational member 18a is provided to be movable relative to the outer periphery surface of the outer cylinder. The following mechanism 18b follows the operation of the operational member 18a. The following mechanism 18b is subjected to the operation of operational member 18a to move the fluid injector 12 between the initial position, the first protrusion position and the second protrusion position in the fluid injector housing space 16c serially.

The following mechanism 18b of the selective transfer mechanism 18 of the operational instrument 14 according to the first embodiment is further configured to return the fluid injector 12 moved to the second protrusion position by the operation of the operational member 18a to the initial position by the next operation of the operational member 18a.

The operational member 18a of the selective transfer mechanism 18 of the operational instrument 14 according to the first embodiment extends to the longitudinal direction of the outer cylinder 6 in the outer periphery surface of the outer cylinder 16. In the operational member 18a, one of extending ends serving as a rotational center, the other extending end can move between a protrusion position (see FIG. 1A) protruding from the outer periphery surface of the outer cylinder 16 and a drawn position where the other extending end is closer to the outer periphery surface of the outer cylinder 16 than it is at the protrusion position.

As shown in FIG. 1A, the fluid injector 12 in the fluid injector housing space 16c of the outer cylinder 16 is positioned at the initial position, while the operational member 18a is positioned at the protrusion portion.

The following mechanism 18b follows a first movement of the operational member 18a from the protrusion position to the drawn position at first to move the fluid injector 12 from the initial position to the first protrusion position in the fluid injector housing space 16c of the outer cylinder 16.

Next, returning the operational member 18a from the drawn position to the protrusion position triggers the following mechanism 18b to move the fluid injector 12 from the first position to the second protrusion position in the fluid injector housing space 16c of the outer cylinder 16, and to keep the fluid injector 12 at the second position.

Further, the following mechanism 18b of this embodiment is moved from the protrusion position to the drawn position again, while the fluid injector 12 is kept at the second protrusion position in the fluid injector housing space 16c of the outer cylinder 16. Thereby, the fluid injector 12 is moved from the second protrusion position to the first protrusion position in the fluid injector housing space 16c of the outer cylinder 16. Next, the operational member 18a is returned from the drawn position to the protrusion position again. The following mechanism 18b follows this to move the fluid injector 12 to the initial position as shown in FIGS. 1A and 1B and to keep the fluid injector 12 at the initial position in the fluid injector housing space 16c of the outer cylinder 16.

The selective transfer mechanism 18 has a forcing unit 20 that forces the fluid injector 12 toward the initial position in the fluid injector housing space 16c of the outer cylinder 16. The movement of the fluid injector 12 in the fluid injector housing space 16c of the outer cylinder 16 from the initial position shown in FIGS. 1A and 1B to the first protrusion position is performed against the force of the forcing unit 20, the movement from the first protrusion position to the second protrusion position is performed by the force of the forcing unit 20, and keeping at the second protrusion position is performed against the force of the forcing unit 20.

Moreover, in the following mechanism 18b, the movement of the fluid injector from the second protrusion position toward the first protrusion position in the fluid injector housing space 16c of the outer cylinder 16 is performed against the force of the forcing unit 20, and the movement from the first protrusion position toward the initial position shown in FIGS. 1A and 1B is performed by the force of the forcing unit 20.

In the operational instrument 14 according to the first embodiment, the fluid injector 12 using the multi-microneedle device 10 is detachably housed in the fluid injector housing space 16c.

A part 16d of an outer periphery wall of the outer cylinder 16 is configured to be detachable. The fluid injector 12 can be attached to or released from the fluid injector housing space 16c of the outer cylinder 16, while the part 16d is released from the rest of the outer periphery wall of the outer periphery 16. It will be noted that, in FIGS. 1A and 1B, the parting line between the detachable part 16d of the outer periphery wall of the outer cylinder 16 and the rest of the outer periphery wall is indicated by the reference symbol 16e.

In this embodiment, the fluid injector 12 has a fluid amount confirmation structure enabling confirmation of the amount of the fluid held in the fluid holding cylinder 12b from the outside. Further specifically, the above-described part 16d of the outer periphery wall of the outer cylinder 16 has a structure enabling observation of the fluid amount confirmation structure of the fluid injector 12 while the above-described part 16d is attached to the rest of the outer periphery of the outer cylinder 16.

Subsequently, the structure of the operational instrument 14 according to the first embodiment is described further in detail, referring to FIGS. 1A and 1B.

The outer cylinder 16 in this embodiment has a first outer cylinder part 22 and a second outer cylinder part 24 fixed at the internal space of the first outer cylinder part 22. The outer periphery surface of the first outer cylinder part 22 provides the outer periphery surface of the outer cylinder 16, and the inner periphery surface of the second outer cylinder part 24 provides the inner periphery surface of the outer cylinder 16. Accordingly, the internal space of the second outer cylinder part 24 provides the fluid injector housing space 16c.

One end 24a of the second outer cylinder part 24 in the direction corresponding to the one opening end 16a of the outer cylinder 16 is protruded outside of the internal space of the first outer cylinder part 22 along the longitudinal axis beyond one end of the first outer cylinder part 22 in the direction corresponding to the one opening end 16a of the outer cylinder 16. The other end 24b of the second outer cylinder part 24 in the direction corresponding to the other opening end 16b of the outer cylinder 16 recedes along the longitudinal axis inside of the internal space of the first outer cylinder part 22 from the other end of the first cylinder part 22 in the direction corresponding to the other opening end 16b of the outer cylinder 16.

Accordingly, in the inner periphery surface of the second outer cylinder part 24, the neighboring part of the one end 24a of the second outer cylinder part 24 in the direction corresponding to the one opening end 16a of the outer cylinder 16 provides the one opening end 16a of the outer cylinder 16. In the inner periphery of the first outer cylinder part 22, the neighboring part of the other end of the first outer cylinder part 22 in the direction corresponding to the other opening end 16b of the outer cylinder 16 provides the other opening end 16b of the outer cylinder 16.

The other opening end 16b of the outer cylinder 16, i.e. the neighboring part of the one end 24a of the second outer cylinder part 24 in the direction corresponding to the one opening end 16a of the outer cylinder 16, in this embodiment, is covered with a detachable lid 25.

The diameter of a part of a portion close to the other opening end 16b, in the inner periphery surface of the periphery wall of the first outer cylinder part 22, is enlarged, and a ring gap is provided between the outer periphery surface of the periphery wall of the second outer cylinder part 24 and the part of the portion close to the other opening end 16b. In this gap 22a, a compression coil spring is disposed. The compression coil spring is wound around the above-described part of the portion, in the outer periphery surface of the periphery wall of the second outer cylinder part 24, close to the other opening end of the outer cylinder 16. In the compression coil spring, a distant end from the other opening end 16b of the outer cylinder 16 is disposed on the bottom of the gap 22a. This compression coil spring serves as the forcing unit 20 in this embodiment.

At a portion close to the one opening end 16a of the outer cylinder 16 in each periphery wall of the first outer cylinder part 22 and the second outer cylinder part 24, the outer cylinder 16 (i.e., each of the first outer cylinder part 22 and the second outer cylinder part 24) is divided into two portions along the longitudinal axis of the outer cylinder 16 (i.e., each of the first outer cylinder part 22 and the second outer cylinder part 24), and the parting line is indicated by the reference symbol 16e.

The divided portions close to the one opening end 16a of the outer cylinder 16 in each periphery wall of the first outer cylinder part 22 and the second outer cylinder part 24 are configured to be detachable from the rest without the above portions by a publicly known detachable structure. The aforementioned portion of each is integrally formed from, for example, transparent synthetic resin, to provide a structure where the inside of the fluid injector housing space 16c of the outer cylinder 16 can be observed.

In the periphery wall of the first outer cylinder part 22, an operational member disposed opening 22b is formed at a part in the vicinity of the other opening end 16b of the outer cylinder 16. In the operational member disposed opening 22b, the operational member 18a of the selection move mechanism 18 is disposed. The operational member disposed opening 22b is defined by a tetragonal shape having a pair of across-the-width sides and a pair of longitudinal sides. In the above periphery wall, the pair of across-the-width sides are separated in the longitudinal direction of the internal space of the first outer cylinder part 22 to face each other, and each extend in a part of the longitudinal direction of the above periphery wall. Each of the pair of longitudinal sides extends in the longitudinal direction of the internal space of the first outer cylinder part 22 to connect to both ends of each of the above pair of across-the-width sides in the above periphery wall.

The operational member disposed opening 22b faces a part at the vicinity of the other opening end 16b of the outer cylinder 16 in the outer periphery surface of the periphery wall of the second outer cylinder part 24 through the gap 22a.

The operational member 18a extends in the longitudinal direction of the internal space of the first outer cylinder part 22, and has one extension end far from the other opening end 16b of the outer cylinder 16 and the other extension end close to the other opening end 16b of the outer cylinder 16. In the operational member 18a, the above one extension end is rotatably supported by the pair of longitudinal sides of the operational member disposed opening 22b of the first outer cylinder part 22. This rotation of the operational member 18a can be carried out between a protrusion position and a drawn position. At the protrusion position, the above other extension end of the operational member 18a protrudes from the operational member disposed opening 22b of the periphery wall of the first outer cylinder part 22 in the outer cylinder 16, as shown in FIG. 1A. At the drawn position, the other extension end of the operational member 18a is forced from the above protrusion position toward the inside of the operational member disposed opening 22b of the periphery wall of the first outer cylinder part 22 in the outer cylinder 16 to be close to the outer periphery surface of the periphery wall of the first outer cylinder parts 22 in the outer cylinder 16.

From the other extension end of the operational member 18a, a pair of arms 18c are protruded along the pair of longitudinal sides of the operational member disposed opening 22b in the gap 22a on both sides of the radial direction of the outer periphery surface of the periphery wall of the second outer cylinder part 24. Projection ends of the pair of arms 18c are configured to be hook portions 18d directed to a direction away from the other opening end 16b of the outer cylinder 16.

A pair of elongate holes 24c are formed on both sides of the above radial direction of the outer periphery surface of the periphery wall of the second outer cylinder part 24. Each of the pair of elongate holes extends from the other end, adjacent to the other opening end 16b of the outer cylinder 16, in the periphery wall of the second outer cylinder wall 24 to a position close to the above-described bottom of the gap 22a along the longitudinal axis of the internal space of the second outer cylinder part 24.

The inner periphery surface of the periphery wall of the second outer cylinder part 24 is enlarged in diameter from a position a predetermined distance away from the one opening end of the one end 24a to the end surface of the other end adjacent to the other opening end 16b of the outer cylinder 16.

A fluid injector holding body 26 is disposed in the region, which is enlarged as described above, of the internal space of the second outer cylinder part 24 providing the fluid injector housing space 16c of the outer cylinder 16. The fluid injector holding body detachably holds the fluid injector 12 using the multi-microneedle device 10 at a predetermined position. The fluid injector holding body 26 is disposed movably along the longitudinal axis of the internal space of the second outer cylinder part 24.

The fluid injector holding body 26 has a pair of protrusions 26a protruding, through the pair of elongate holes 24c of the second outer cylinder part 24, inside the gap 22a between the outer periphery surface of the second outer cylinder part 24 and the aforementioned enlarged region of the inner periphery surface of the first cylinder part 22. The pair of protrusions 26a are put on the end, which is close to the other opening end 16b of the outer cylinder 16, of the compression coil spring which is wound around the outer periphery surface of the second outer cylinder part 24, disposed as described above, and serves as the forcing unit 20 in this embodiment. That is, the compression coil spring can be compressed between the pair of protrusions 26a of the fluid injector holding body 26 and the aforementioned bottom of the gap 22a.

The aforementioned following mechanism 18b of the selective transfer mechanism 18 is disposed at the other end, which faces the other opening end 16b of the outer cylinder 16 (in this case, the first outer cylinder part 22), of the fluid injector holding body 26. The following mechanism 18b has a pair of protrusions 18e protruding, through the pair of elongate holes 24c, inside the gap 22a between the outer periphery surface of the second outer cylinder part 24 and the aforementioned enlarged region of the inner periphery surface of the first cylinder part 22.

As shown in FIGS. 1A and 1B, the hook portions are hooked on the pair of protrusions 18e of the following mechanism 18b. As a result, the fluid injector holding body 26 is pressed through the following mechanism 18b toward a portion adjacent to the one end 24a, on the direction corresponding to the one opening end 16a of the outer cylinder 16, of the second outer cylinder part 24 in the inner periphery surface of the second outer cylinder part 24. The fluid injector holding body 26 is kept at an initial position as shown in FIGS. 1A and 1B in a state where the forcing unit 20 is compressed by the pair of protrusions 26a, i.e., a state where the fluid injector holding body 26 withstands against the accumulated force in the forcing unit 20.

The end face 26b, which faces the one end 24a of the second outer cylinder part 24, in the fluid injector holding body is separated from the bottom, which is close to the one end 24a of the second outer cylinder 24, in the enlarged region of the inner periphery surface of the internal space of the second outer cylinder part 24 toward a direction away from the above one end 24a, by a predetermined distance, when the fluid injector holding body 26 is disposed at the above initial position.

The fluid injector holding body 26 is also divided in to two portion along the longitudinal axis of the fluid injector holding body 26 by a parting line. The above parting line of the fluid injector holding body 26 is along the parting line 16e of the outer cylinder 16 (i.e., each of the first outer cylinder part 22 and the second outer cylinder part 24), when the fluid injector holding body 26 is disposed at the above initial position. At this time, a part of the fluid injector holding body 26 is detachable from the rest owing to having a detachable structure.

This part of the fluid injector holding body 26 is integrally formed from transparent materials (for example, a transparent synthetic resin). Forming the aforementioned one of two divided parts of the outer cylinder 16 (i.e., of each of the first outer cylinder part 22 and the second outer cylinder part 24) from transparent materials (for example, a transparent synthetic resin) integrally provides a structure by which the fluid injector 26 held by the fluid injector holding body 26 can be observed.

That is, in the operational instrument 14 of this embodiment, when the fluid injector holding body 26 is disposed at the above initial position, the fluid injector 12 held by the fluid injector holding body 26 can be observed through the portion of transparent materials divided by the parting line 16e in the outer cylinder 16 (i.e., each of the first outer cylinder part 22 and the second outer cylinder part 24) and the part of transparent materials divided by the aforementioned parting line along the parting lie 16e in the fluid injector holding body 26.

In this embodiment, the fluid holding cylinder 12b of the fluid injector 12 is also formed from transparent materials (for example, a transparent synthetic resin). As a result, it has a fluid amount confirmation structure by which the amount of the fluid held in the fluid holding cylinder 12 can be observed from the outside.

A fluid holding cylinder hold trench 26b for holding the fluid injector 12 is formed at the inside of the fluid injector holding body 26 concentrically with the longitudinal axis of the fluid injector holding body 26. The fluid holding cylinder hold trench 26b has an inner periphery surface which is the same as the outer periphery surface of a portion at the vicinity of the piston member 12c in the fluid holding cylinder 12b of the fluid injector 12. The fluid holding cylinder hold trench 26b is divided into two parts along the aforementioned parting line of the fluid injector holding body 26. Further, at the inside of the fluid injector holding body 26, a piston member housing trench 26c is serially formed to the fluid holding cylinder hold trench 26b on the other opening end 16b side of the first outer cylinder part 22 of the outer cylinder 16. The piston member housing trench 26c houses the piston member 12c movable relative to the fluid holding cylinder 12b of the fluid injector 12, when the fluid holding cylinder hold trench 26b of the fluid injector 12 is held by the fluid holding cylinder hold trench 26b.

Accordingly, in the operational instrument 14 of this embodiment, when the fluid injector holding body 26 is disposed at the above initial position, the portion of transparent materials, which is divided by the parting line 16e, in the outer cylinder 16 (i.e., each of the first outer cylinder part 22 and the second outer cylinder part 24) and the part of transparent materials, which is divided by the aforementioned parting line along the parting line 16e, in the fluid injector holding body 26 can be detached from the other portion, which is divided by the parting line 16e, in the outer cylinder 16 (i.e., each of the first outer cylinder part 22 and the second outer cylinder part 24) and the other part, which is divided by the aforementioned parting line along the parting line 16e, in the fluid injector holding body 26. Thereafter, the fluid holding cylinder 12b and the piston member 12c of the fluid injector 12 can be held in the remaining half of the fluid holding cylinder hold trench 26b and the half of the piston member housing trench 26c of the fluid injector holding body 26 detachably.

As shown in FIGS. 1A and 1B, the fluid holding cylinder 12 has a flange 12d, and the fluid holding cylinder 12b is held in the fluid holding cylinder hold trench 26b of the fluid injector holding body 26. This prevents the fluid holding cylinder 12b from moving along the longitudinal axis of the fluid injector holding body 26 relative to the fluid injector holding body 26.

As shown in FIGS. 1A and 1B, when the fluid injector holding body 26 is disposed at the initial position in the fluid injector housing space 16c of the outer cylinder 16 (in this case, the second outer cylinder part 24), in the multi-microneedle device 10 attached to the fluid outflow port 12a of the fluid injector 12, the skin contact surface 10d of the main body 10b with the plurality of microneedles 10c is retracted into the fluid injector housing space 16c from the one opening end 16a of the outer cylinder 16 (in this case, the second outer cylinder part 24).

A piston member pressing rod 28 for pressing the piston member 12c of the fluid injector 12 is inserted into the piston member housing trench 26 of the fluid injector holding body 26 from the outside of the lid 25 covering the other opening end 16b of the outer cylinder 16 (in this case, the first outer cylinder part 22). The piston member pressing rod 28 penetrates the following mechanism 18b and the end of the fluid injector holding body 26 facing the following mechanism 18b along the longitudinal axis of the outer cylinder 16 (in this embodiment, the first outer cylinder part 22 and the second outer cylinder part 24) to extend to the piston member housing trench 26. The piston member pressing rod 28 is movable relative to the lid 25, the following mechanism 18b and the fluid injector holding body 26 along the longitudinal axis of the outer cylinder 16 (in this embodiment, each of the first outer cylinder part 22 and the second outer cylinder part 24).

The piston member pressing rod 28 has a fine length regulation mechanism 28a in the piston member housing trench 26. In this embodiment, the fine length regulation mechanism 28a includes a length fine regulation member threadably mounted on an inner end of the piston member pressing rod 28 in the piston member housing trench 26. The length fine regulation member extends from the inner end of the piston member pressing rod 28 along the longitudinal axis further inward, and moves relative to the inner end of the piston member pressing rod 28 toward one direction or the other direction along the longitudinal axis of the piston member pressing rod 28, depending on a direction to which it rotates around the longitudinal axis of the piston member pressing rod 28 relative to the inner end of the piston member pressing rod 28.

The length fine regulation member includes a fine length regulation dial 28b whose diameter is enlarged toward the radial direction of the piston member pressing rod 28 in the piston member housing trench 26 of the fluid injector holding body 26. The length fine regulation member with the piston member pressing rod 28 is forced toward a direction where they protrude from the lid 25 to the external space by a sub forcing unit 28c arranged in the piston member housing trench 26 of the fluid injector holding body 26.

In detail, in this embodiment, the sub forcing unit 28c is configured from a compression coil spring wound around the length fine regulation member. One end of this compression coil spring contacts the fine length regulation dial 28b, the other end contacts a step which is formed separately toward a direction to the inner end of the piston member pressing rod 28 along the longitudinal axis of the piston member pressing rod 28 in the inner periphery surface of the piston member housing trench 26 of the fluid injector holding body 26.

The movement to a direction from the lid 25 to the external space of the length regulation member with the fine length regulation dial 28b due to the force of the sub forcing unit 28c is stopped by the contact of the fine length regulation dial 28b with the step which is formed on the following mechanism 18b side in the inner periphery surface of the piston member housing trench 26 of the fluid injector holding body 26, as shown in FIG. 1B. The position of the piston member pressing rod 28 relative to the fluid injector holding body 26 at this time is the protrusion position.

A length fine regulation dial operation window is formed at the periphery wall of the fluid injector holding body 26. The length fine regulation dial operation window can reach a part of the outer periphery surface of the fine length regulation dial 28b at the protrusion position from radially outside.

In this embodiment, the fine regulation of length of the piston member pressing rod 28 is performed with the fine length regulation dial 28b of the length fine regulation member of the piston member pressing rod 28, as follows.

At first, the lid 25 is removed from the other opening end 16b of the outer cylinder 16, of the first outer cylinder part 22 in this embodiment. Next, the protrusions 18e of the operational member 18a of the selective transfer mechanism 18 are released from the hook portion 18d of the pair of arms 18c of the operational member 18a of the selective transfer mechanism 18. Thereafter, the outer periphery surface of the aforementioned fine length regulation dial 28b of the piston member pressing rod 28 disposed at the aforementioned protrusion position as described above is rotated toward one direction or the other direction of the circumferential direction of the fine length regulation dial 28b through the aforementioned length fine regulation dial operation window of the periphery wall of the fluid injector holding body 26 taken toward the external space.

In this embodiment, the following mechanism 18b which the piston member pressing rod 28 penetrates includes, in the fluid injector holding body 26, a rotating cam RC and a rotating cam rotation drive member DM. The rotating cam RC is put on the other end facing the other opening end 16b of the outer cylinder 16 (in this case, of the first outer cylinder part 22), and has a publicly known configuration. The rotating cam rotation drive member DM is disposed adjacent to the rotating cam RC on the opposite side to the other end of the fluid injector holding body 26, and has a publicly known configuration. The afore mentioned pair of protrusions 18e are formed in the rotating cam rotation drive member DM, and the rotating cam RC has the capacity to rotate concentrically relative to the piston member pressing rod 28.

Pushing the operational member 18a away from the protrusion position shown in FIG. 1A to the aforementioned drawn position causes the hook portions 18d of the protrusion ends in the pair of arms 18c of the operational member 18a to load pressing force toward the one opening end 16a of the outer cylinder 16 (in this case, of the one end 24a of the second outer cylinder 24) on the pair of protrusions 18e the rotating cam rotation drive member DM.

The pressing force is transmitted through the rotating cam rotation drive member DM and the rotating cam RC to the fluid injector holding body 26. As a result, the fluid injector holding body 26 with the rotating cam rotation drive member DM, the rotating cam RC and the piston member pressing rod 28 penetrating these moves toward the one opening end 16a of the outer cylinder 16 (in this case, of the one end 24a of the second outer cylinder part 24) against the force of the forcing unit 20 in the fluid injector housing space 16c (in this case, the internal space of the second outer cylinder part 24) of the outer cylinder 16.

When the aforementioned push to the operational member 18a is released, the pressing force toward the one end 16a of the outer cylinder 16 (in this case, of the one end 24a of the second outer cylinder part 24) on the pair of protrusions 18e of the rotating cam rotation drive member DM from the hook portions 18d at the protrusion ends of the pair of arms 18c of the operational member 18a is also released.

As a result, the fluid injector holding body 26 with the rotating cam rotation drive member DM, the rotating cam RC and the piston member pressing rod 28 is subjected to the force of the forcing unit 20 in the fluid injector housing space of the outer cylinder 16, the internal space of the second outer cylinder part 24 in this embodiment, to move from the one opening end 16a of the outer cylinder 16 (in this embodiment, of the second outer cylinder part 24) toward the other opening end 16b of the outer cylinder 16 (in this embodiment, of the first outer cylinder part 22).

The rotating cam rotation drive member DM and the rotating cam RC is configured such that, by pushing the operational member 18a from the protrusion position shown in FIG. 1A to the aforementioned drawn position once, the rotating cam rotation drive member DM rotates the rotating cam RC, on which the force of the forcing unit 20 is loaded through the fluid injector holding body 26, around the piston member pressing rod 28 toward a predetermined circumferential direction by a predetermined rotation angle. Such a structure of the rotating cam rotation drive member DM and the rotating cam RC is publicly known.

While the operational member 18a is disposed at the protrusion position shown in FIG. 1A, the hook portions 18d at the protrusion ends of the pair of arms 18c of the operational member 18a are hooked on the pair of protrusions 18e of the rotating cam rotation drive member DM of the following mechanism 18b, and the fluid injector holding body 26 with the rotating cam rotation drive member DM, the rotating cam RC and the piston member pressing rod 28 penetrating these is disposed against the force of the forcing unit 20 at the initial position shown in FIG. 1A in the fluid injector housing space 16c (in this case, the internal space of the second outer cylinder part 24). The skin contact surface 10d and the microneedles 10c of the main body 10b of the multi-microneedle attached, as described above, to the fluid injector 12 held by the fluid injector holding body 26 is drawn from the one opening end 16a of the outer cylinder 16 (in this case, of the one end 24a of the second outer cylinder part 24) into the fluid injector housing space 16c (in this case, the internal space of the second outer cylinder part 24), as shown in FIG. 1A.

Next, the operational member 18a is pushed from the protrusion position shown in FIG. 1A to the aforementioned drawn position. This causes the hook portions 18d at the protrusion ends of the pair of arms 18c of the operational member 18a to load pressing force toward the one opening end 16a of the outer cylinder 16 (in this case, of the one end 24a of the second outer cylinder part 24) on the pair of protrusions 18e of the rotation cam rotation drive member DM.

This pressing force is transmitted to the fluid injector holding body 26 through the rotating cam rotation drive member DM and the rotating cam RC. As a result, the fluid injector holding body 26 with the rotating cam rotation drive member DM, the rotating cam RC and the piston member pressing rod 28 penetrating these is moved in the fluid injector housing space 16c, the internal space of the second outer cylinder part 24 in this embodiment, against the force of the forcing unit 20 toward the one opening end 16a of the outer cylinder 16 (in this case, of the one end 24a of the second outer cylinder part 24). During this, the rotating cam rotation drive member DM rotates the rotating cam RC from an initial position hold position to a second protrusion position hold position by the aforementioned predetermined rotation angle toward the aforementioned predetermined circumferential direction around the piston member pressing rod 28.

At this time, the skin contact surface 10d and the microneedles 10c of the main body 10b of the multi-microneedle device 10 attached, described above, to the fluid injector 12 held by the fluid injector holding body 26 are disposed at the first protrusion position where they are protruded by the first distance from the one opening end 16a of the outer cylinder 16 (in this embodiment, of the one end 24a of the second outer cylinder part 24) toward the external space.

When the aforementioned push to the operational member 18a is released, the pressing force loaded on the pair of protrusions 18e of the rotating cam rotation drive member DM by the hook portions 18d at the protrusion ends of the pair of arms 18c of the operational member 18a, toward the one opening end 16a of the outer cylinder 16 (in this case, of the one end 24a of the second outer cylinder part 24) is released. As a result, the fluid injector holding body 26 with the rotating cam rotation drive member DM, the rotating cam RC and the piston member pressing rod 28 penetrating these is moved in the fluid injector housing space 16c (in this case, the internal space of the second outer cylinder part 24) of the outer cylinder 16, owing to the force of the forcing unit 20, from the one end 16a of the outer cylinder 16 (in this case, of the one end 24a of the second outer cylinder part 24) toward the other opening end 16b of the outer cylinder 16 (in this case, of the first outer cylinder part 22). The fluid injector holding body 26, however, does not return to the aforementioned initial position because the action of the combination of the rotating cam rotation drive member DM and the rotating cam RC, the aforementioned movement is stopped and the stop state is held.

At this time, the skin contact surface 10d and the microneedles 10c of the main body 10b of the multi-microneedle device attached, as described above, to the fluid injector 12 held by the fluid injector holding body 26 are disposed at the second protrusion position where they are protruded by the second protrusion distance shorter than the first protrusion distance from the one end 16a of the outer cylinder 16 (in this case, of the one end 24a of the second outer cylinder part 24) to the external space, and are held at the second protrusion position by the action of the combination of the rotating cam rotation drive member DM and the rotating cam RC.

Further, the operational member 18a is pushed from the protrusion position shown in FIG. 1A to the aforementioned drawn position again. This causes the hook portions 18d at the protrusion ends of the pair of arms 18c of the operational member 18a to load pressing force toward the one opening end 16a of the outer cylinder (in this case, the one end 24a of the second outer cylinder part 24) on the pair of protrusions 18e of the rotating cam rotation drive member DM.

The pressing force is transmitted to the fluid injector holding body 26 through the rotating cam rotation drive member DM and the rotating cam. As a result, the fluid injector holding body 26 with the rotating cam rotation drive member DM, the rotating cam RC and the piston member pressing rod 28 penetrating these is moved in the fluid injector housing space 16c (in this case, the internal space of the second outer cylinder part 24) against the force of the forcing unit 20 toward the one opening end 16a of the outer cylinder 16 (in this case, of the one end 24a of the second outer cylinder part 24). During this, the rotating cam rotation drive member DM further rotates the rotating cam RC from the aforementioned second protrusion position hold position to the aforementioned initial position hold position by the aforementioned predetermined rotation angle toward the aforementioned predetermined circumferential direction around the piston member pressing rod 28.

At this time, the skin contact surface 10d and the microneedles 10c of the main body 10b of the multi-microneedle device attached, as described above, to the fluid injector 12 held by the fluid injector holding body 26 are moved toward the first protrusion position where they are protruded by the first distance from the one opening end 16a of the outer cylinder 16 (in this case, of the one end 24a of the second outer cylinder part 24) toward the external space.

Furthermore, when the aforementioned push to the operational member 18a is released, the pressing force loaded on the pair of protrusions 18e of the rotating cam rotation drive member DM by the hook portions 18d at the protrusion ends of the pair of arms 18c of the operational member 18a, toward the one opening end 16a of the outer cylinder 16 (in this case, of the one end 24a of the second outer cylinder part 24) is released. As a result, the fluid injector holding body 26 with the rotating cam rotation drive member DM, the rotating cam RC and the piston member pressing rod 28 penetrating these is moved in the fluid injector housing space 16c (in this case, the internal space of the second outer cylinder part 24) of the outer cylinder 16, owing to the force of the forcing unit 20, from the one opening end 16a of the outer cylinder 16 (in this case, of the one end 24a of the second outer cylinder part 24) toward the other opening end 16b of the outer cylinder 16 (in this case, of the first outer cylinder part 22)(i.e., toward from the first protrusion position to the aforementioned initial position), and returned to the aforementioned initial position. Thus, the fluid injector holding body 26 is held at the initial position by the rotating cam RC at the aforementioned initial position hold position.

At this time, the skin contact surface 10d and the microneedles 10c of the main body 10b of the multi-microneedle device attached, as described above, to the fluid injector 12 held by the fluid injector holding body 26 are drawn from the one opening end 16a of the outer cylinder 16 (in this case, of the one end 24a of the second outer cylinder part 24) into the fluid injector housing space 16c (in this case, the internal space of the second outer cylinder part 24) of the outer cylinder 16.

Henceforth:

The first round of the combination of the movement of the operational member 18a from the protrusion position shown in FIG. 1A to the drawn position and the movement from the aforementioned drawn position to the aforementioned protrusion position allows the skin contact surface 10d and the microneedles 10c of the main body 10b of the multi-microneedle device attached, as described above, to the fluid injector 12 held by the fluid injector holding body 26 to be moved from the aforementioned initial position to the first protrusion position, to be moved from the first protrusion position to the second protrusion position, and to be held at the second protrusion position; and following to this, by the second round of the movement of the operational member 18a from the protrusion position shown in FIG. 1A to the aforementioned drawn position and the movement of the operational member 18a from the aforementioned drawn position to the aforementioned protrusion position, the skin contact surface 10d and the microneedles 10c of the main body 10b of the multi-microneedle device attached, as described above, to the fluid injector 12 held by the fluid injector holding body 26 are moved from the aforementioned second protrusion position to the aforementioned first protrusion position, thereafter moved from the aforementioned first protrusion position to the aforementioned initial position, and held at the aforementioned initial position;

these are serially repeated.

With reference to FIG. 2A, FIG. 2B, FIG. 2C and FIG. 2D in addition to FIG. 1A and FIG. 1B, next is described a procedure of injecting the fluid (for example, medicinal solution) held in the fluid injector 12 to skin tissue at a desired site where the skin of a living thing (in this embodiment, for example, a human being) is exposed, operating the fluid injector 12 using the multi-microneedle device 10 with the operational instrument 14 according to the first embodiment, mentioned above referring to FIG. 1A and FIG. 1B.

At first, a user of the operational instrument 14 according to the aforementioned first embodiment of this embodiment detaches a part of the transparent materials, which is divided by the parting line 16e, of the outer cylinder 16 (i.e., each of the first outer cylinder part 22 and the second outer cylinder part 24) and a part of the transparent materials, which is divided by the aforementioned parting line along the parting line 16e, of the fluid injector holding body 26 from the other part, which is divided by the parting line 16e, of the outer cylinder 16 (i.e., each of the first outer cylinder part 22 and the second outer cylinder part 24) and the other part, which is divided by the aforementioned parting line along the parting line 16e, of the fluid injector holding body 26, while the operational member 18a of the selective transfer mechanism 18 is disposed at the protrusion position as shown in FIG. 1A, the fluid injector holding body 26 is disposed at the initial position as shown in FIG. 1A and the piston member pressing rod 28 is disposed at the protrusion position.

Subsequently, the fluid holding cylinder 12b and the piston member 12c of the fluid injector 12 attached to the multi-microneedle device 10 is made to be held by the other part of the fluid injector holding body 26 exposed outside described above, the half of the fluid holding cylinder hold trench 26b and the half of the piston member housing trench 26c (see FIG. 1B).

Until this time, the fluid holding cylinder 12b, the fluid holding space of the main body 10a of the multi-microneedle device 10, and the fine fluid injection passages of the plurality of microneedles 10c of the multi-microneedle device 10 have already been filled with a desired amount of the fluid (for example, medicinal solution) for injecting to the skin tissue of the living thing (for example, a human being).

Next, the part of the transparent materials, which is divided by the aforementioned parting line along the parting line 16e and detached as described above, of the fluid injector holding body 26 is detachably attached to the other part, and the fluid holding cylinder 12b and piston member 12c of the fluid injector 12 are covered with the part of the transparent materials and the other part.

Further, the part of the transparent materials, which is divided by the parting line 16e and detached as described above, of the outer cylinder 16 (i.e., each of the first outer cylinder part 22 and the second outer cylinder part 24) is detachably attached to the other part (see FIG. 1A).

At this time, the skin contact surface 10d and the plurality of microneedles 10c of the main body 10b of the multi-microneedle device 10 attached to the fluid injector 12 held by the fluid injector holding body 26 disposed at the initial position as described above are drawn from the one opening end 16a of the outer cylinder 16 (in this case, of the one end 24a of the second outer cylinder part 24) inside of the fluid injector housing space 16c of the outer cylinder 16 (in this case, of the second outer cylinder part 24).

After this, the user holds the outer periphery surface (in this case, the outer periphery surface of the first outer cylinder part 22) of the outer cylinder 16, avoiding the contact with the operational member 18a, at the aforementioned protrusion position, of the selective transfer mechanism 18. Subsequently, the user presses the one opening end 16a of the outer cylinder 16 (in this embodiment, the one opening end 16a of the one end 24a of the second outer cylinder part 24) to the desired and exposed site of the skin SK of the living thing (for example, a human being).

Figure 2A:
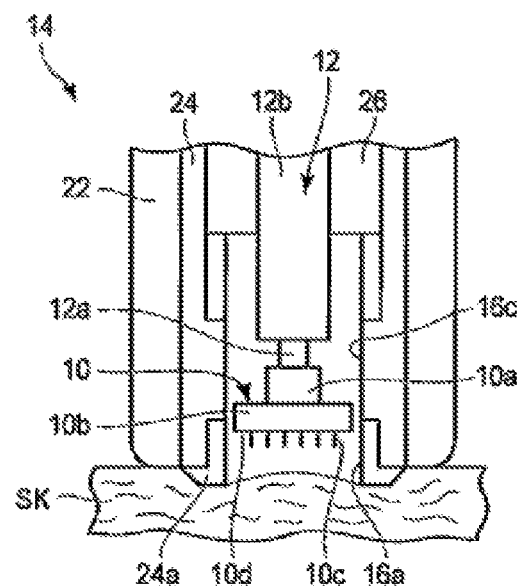
FIG. 2A is a schematic and enlarged longitudinal sectional view showing a part of the outer cylinder of the operational instrument and the fluid injector using a multi-microneedle device disposed at an initial position. The view shows a state where the fluid injector using the multi-microneedle device disposed at the initial position in the outer cylinder of the operational instrument is positioned by the operational instrument shown in FIG. 1A and FIG. 1B, according to the first embodiment, at a desired site of exposed skin of a living thing.

At this time, the desired and exposed site of the skin SK is pressed inside the skin SK by the periphery (in this case, the end face of the one end 24a of the second outer cylinder part 24) of the one opening end 16a of the outer cylinder 16, thereby only the region surrounded by the one opening end 16a expands outside the skin SK in some degree because of elasticity of the skin SK (see FIG. 2A).

Subsequently, the operational member 18a of the selective transfer mechanism 18 is pushed to be moved from the aforementioned protrusion position to the aforementioned drawn position. The movement is transmitted to the following mechanism 18b of the selective transfer mechanism 18. As a result, the following mechanism 18b moves the fluid injector holding body 26 toward the one opening end 16a of the outer cylinder 16 (of the one end 24a of the second outer cylinder part 24 in this embodiment). Thus, the skin contact surface 10d and the plurality of microneedles 10c of the main body 10b of the multi-microneedle device 10 attached to the fluid injector 12 held by the fluid injector holding body 26 are moved to the first protrusion position where they are protruded by the first distance from the one end 16a (in this case, of the one end 24a of the second outer cylinder part 24) of the outer cylinder 16 toward the external space.

Figure 2B:
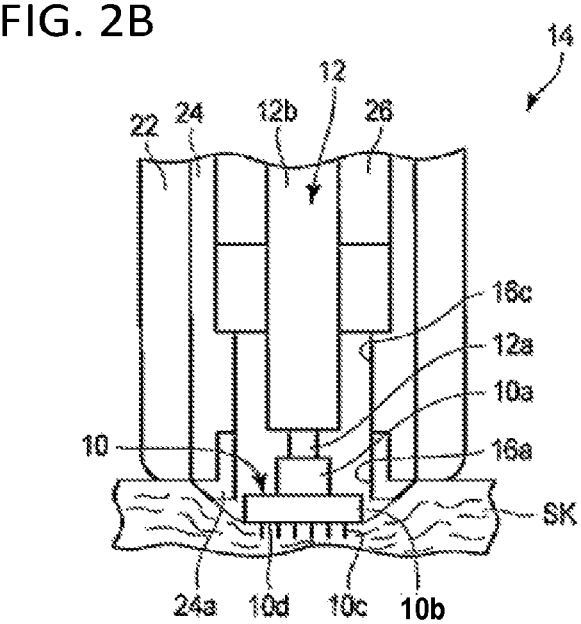
FIG. 2B is a schematic and enlarged longitudinal sectional view showing a part of the outer cylinder of the operational instrument and the fluid injector using a multi-microneedle device disposed at an initial position. The view shows a state where the fluid injector using the multi-microneedle device is moved from the initial position of FIG. 2A to a first protrusion position in the outer cylinder of the operational instrument by a selective transfer mechanism of the operational instrument, while the operational instrument shown in FIG. 1A and FIG. 1B, according to the first embodiment, is positioned at the desired site of exposed skin of a living thing as shown in FIG. 2A.

The skin contact surface 10d of the main body 10b of the multi-microneedle device 10 moved at the first protrusion position presses strongly the region surrounded by the one opening end 16a of the outer cylinder 16 (in this case, of the second outer cylinder part 24) at the desired and exposed site of the skin SK such that the plurality of microneedles 10c reliably pierce the skin tissue at the region (see FIG. 2B).

At this time, the elasticity of the above skin tissue at the aforementioned desired site of the exposed skin SK is reduced in some degree.

Next, the pressing force loaded on the operational member 18a of the selective transfer mechanism 18 is released to return the operational member 18a from the aforementioned drawn position to the aforementioned protrusion position. The movement of the operational member 18a moves the fluid injector holding body 26 toward the one opening end 16a of the outer cylinder 16 (in this case, of the one end 24a of the second outer cylinder part 24). This movement, however, is stopped by the following mechanism 18b of the selective transfer mechanism 18, before reaching the aforementioned initial position, at the point when the skin contact surface 10d and the plurality of microneedles 10c of the main body 10b of the multi-microneedle device 10 attached to the fluid injector 12 held by the fluid injector holding body 26 reach the second protrusion position where they are protruded by the second distance which is shorter than the first distance from the one opening end 16a of the outer cylinder 16 (in this embodiment, of the one end 24a of the second outer cylinder part 24) toward the external space. The skin contact surface 10d and the plurality of microneedles 10c are held at the protrusion position.

The skin contact surface 10d of the main body 10b of the multi-microneedle device 10 moved to the second protrusion position weakens the pressing force to the region surrounded by the one opening end 16a of the outer cylinder 16 (in this case, the second outer cylinder part 24). The recovery of the elasticity allows the above region to follow the skin contact surface 10d. As a result, the skin contact surface 10d can keep contacting the above region, and piercing the above region by the plurality of microneedles 10c is kept (see FIG. 2C).

The user presses an external exposed end of the piston member pressing rod 28, disposed at the protrusion position as described above, of the operational instruments 14 to force the piston member 12c of the fluid injector 12 through the fine length regulation mechanism 28a of the inner end of the piston member pressing rod 28, while the multi-microneedle device 10 is held at the second protrusion position as described above. As a result, the fluid filling the fluid holding cylinder 12b of the fluid injector 12, the fluid holding space of the main body 10a of the multi-microneedle device 10 and the fine fluid injection passage of many microneedles 10c described above can easily and quickly be injected, through the fine fluid injection passages of many microneedles 10c, inside the skin tissue of the aforementioned region, where the elasticity is recovered as described above, at the aforementioned desired position where the skin SK is exposed the depending on the distance of pressing without leaking outside the skin SK as shown by multiple arrows in FIG. 2D.

The user can easily confirm the injection amount of the aforementioned fluid through the part of the transparent materials, which is divided by the parting line 16e, of the outer cylinder 16 (i.e., each of the first outer cylinder part 22 and the second outer cylinder part 24) of the operational instrument 14 and the part of the transparent materials, which is divided by the parting line along the parting line 16e, of the fluid injector holding body 26, by observing the fluid holding cylinder 12b of the fluid injector 12.

After finishing the injection from the fluid injector 12 through many microneedles of the multi-microneedle device 10 inside the skin tissue of the aforementioned region at the aforementioned desired site where the skin SK is exposed, the operational instrument 14 is separated from the aforementioned desired site where the skin SK is exposed, and the multi-microneedle device 10 is pulled out from the skin tissue of the aforementioned region at the aforementioned desired site where the skin SK at the same time.

It will be noted that the following operation may be performed before separating the operational instrument 14 from the aforementioned desired site where the skin SK is exposed.

The operational member 18a of the selective transfer mechanism 18 is pushed again to be moved from the aforementioned protrusion position to the aforementioned drawn position. This movement of the operational member 18a is transmitted to the following mechanism 18b. The following mechanism 18b moves the fluid injector fold body 26 toward the one opening end 16a of the outer cylinder (in this case, of the one end 24a of the second outer cylinder 24). Thereby, the skin contact surface 10d and the plurality of microneedles 10c of the main body 10b of the multi-microneedle device 10 attached to the fluid injector held by the fluid injector holding body 26 is moved from the aforementioned second protrusion position to the aforementioned first protrusion position.

Subsequently, the pressing force loaded on the operational member 18 of the selective transfer mechanism 18 is released to return the operational member 18a from the aforementioned drawn position to the aforementioned protrusion position. This movement of the operational member 18a moves the fluid injector holding body 26 toward the one opening end 16a of the outer cylinder (in this case, of the one end 24a of the second outer cylinder part 24), stops when the fluid injector holding body 26 reaches the aforementioned initial position, and holds the fluid injector holding body 26 at the aforementioned initial position (see FIG. 2A).

Figure 2C:
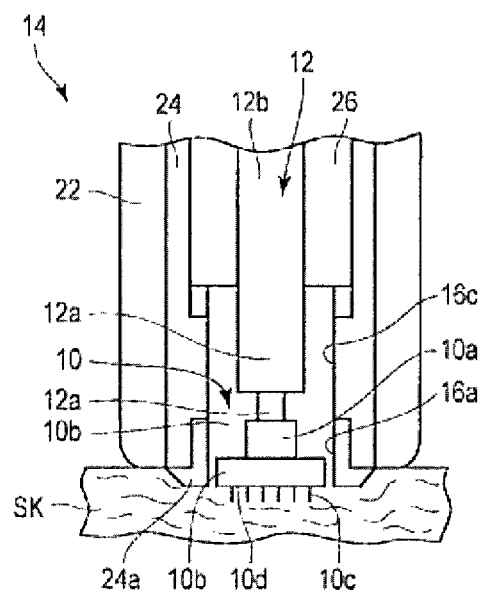
FIG. 2C is a schematic and enlarged longitudinal sectional view showing a part of the outer cylinder of the operational instrument and the fluid injector using a multi-microneedle device disposed at an initial position. The view shows a state where the fluid injector using the multi-microneedle device is moved from the first protrusion position of FIG. 2B to a second protrusion position in the outer cylinder of the operational instrument by a selective transfer mechanism of the operational instrument, while the operational instrument shown in FIG. 1A and FIG. 1B, according to the first embodiment, is positioned at the desired site of exposed skin of a living thing as shown in FIG. 2A.
Figure 2D:
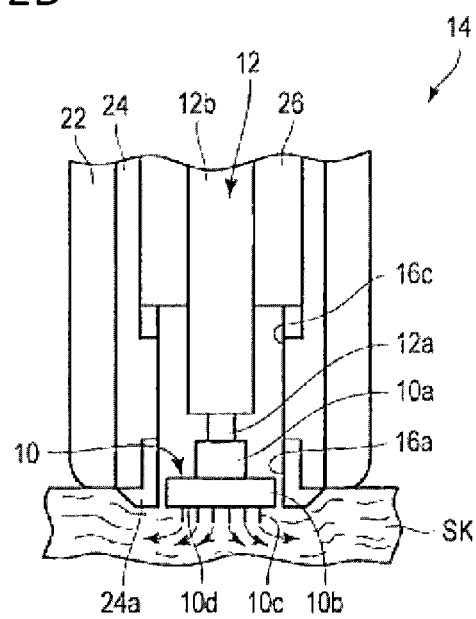
FIG. 2D is a schematic and enlarged longitudinal sectional view showing a part of the outer cylinder of the operational instrument and the fluid injector using a multi-microneedle device disposed at an initial position. The view shows a state where a fluid held in a fluid holding cylinder is injected from the fluid injector through a plurality of microneedles of the multi-microneedle device into skin tissue at the desired site of exposed skin of a living thing, while the operational instrument shown in FIG. 1A and FIG. 1B, according to the first embodiment, is positioned at the desired site of exposed skin of a living thing as shown in FIG. 2A and the fluid injector using the multi-microneedle device is moved to the second protrusion position shown in FIG. 2C in the outer cylinder of the operational instrument by the selective transfer mechanism of the operational instrument.

In the aforementioned embodiment, the user presses the external exposed end of the piston member pressing rod 28, which is disposed at the protrusion position as described above, of the operational instrument 14, while the multi-microneedle device 10 is held at the second protrusion position as shown in FIG. 2C. Alternatively, at this time, pressing the external exposed end of the piston member pressing rod 28, which is disposed at the protrusion position as described above, of the operational instrument 14 may be carried out by a fluid injector selective drive unit 30, as shown in FIG. 1A.

Such a fluid injector selective drive unit 30 can be fixed detachably at the vicinity of the other opening end 16 in the outer periphery surface of the outer cylinder 16, and is configured to press the external exposed end of the piston member pressing rod 28 disposed at the protrusion position as described above. This configuration can include a drive member not shown in the drawings, a force generation source not shown in the drawings, and a switching mechanism not shown in the drawings. The drive member contacts the external exposed end of the piston member pressing rod 28. The force generation source gives the drive member force toward the external exposed end of the piston member pressing rod 28. The switching mechanism makes the force generation mechanism not shown in the drawings generate the force selectively.

Further specifically, for example, the force generation source not shown in the drawings can be selected from a compression spring, an extension spring, an elastic material, and a supply source of compressed gas including compressed air. The switching mechanism can be a publicly known latch mechanism, trigger mechanism or push clasp mechanism keeping stopping the movement against the force generated from the force generation source, or a manual-powered or electromagnetically-driven ON-OFF valve that can selectively supply the drive member not shown in the drawings the compressed gas including compressed air from a compressed gas supply source.

Second Embodiment

Figure 3A:
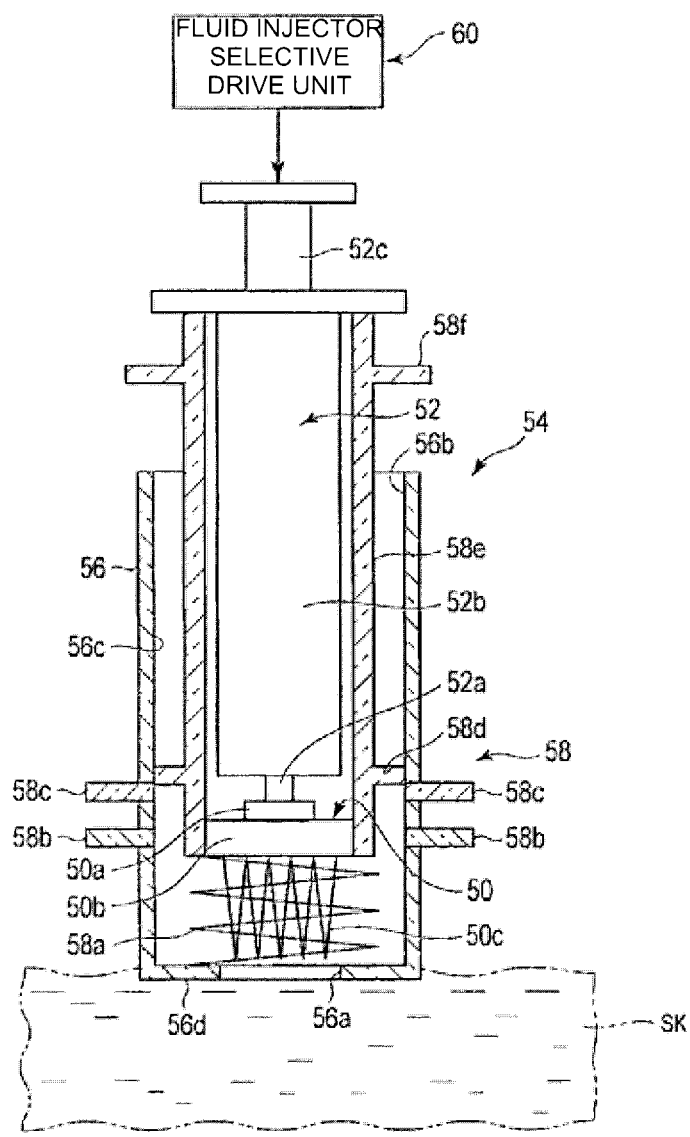
FIG. 3A is a schematic longitudinal sectional view of an operational instrument, for a fluid injector using a multi-microneedle device, according to a second embodiment, and here the fluid injector using the multi-microneedle device is disposed at an initial position in an outer cylinder of the operational instrument by a selective transfer mechanism.
Figure 3B:
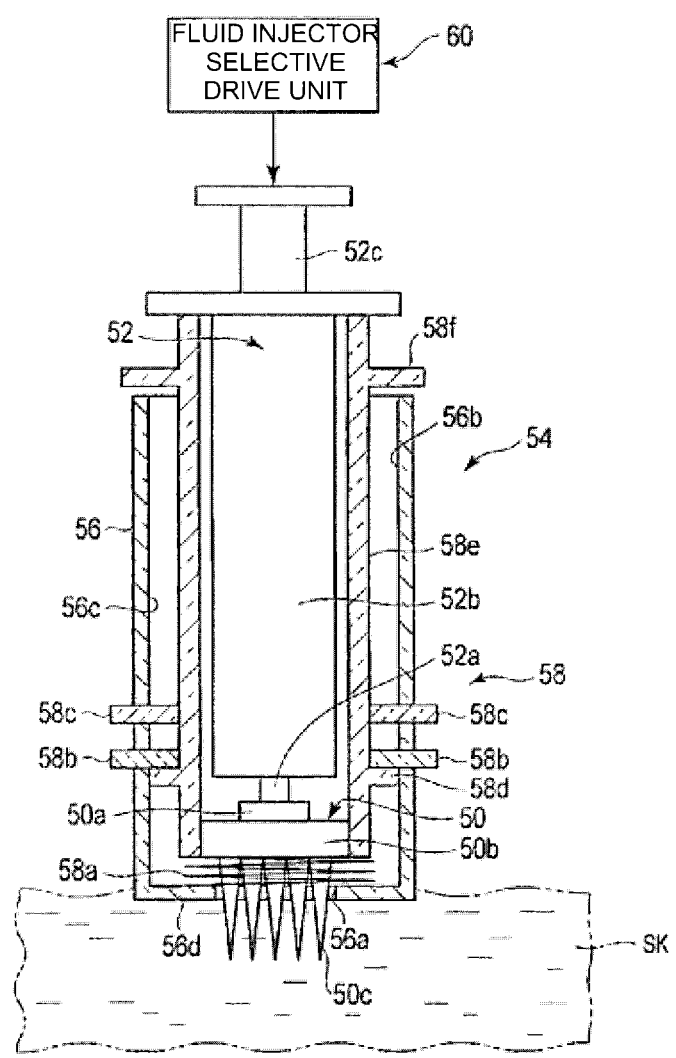
FIG. 3B is a schematic longitudinal sectional view of the operational instrument, for a fluid injector using a multi-microneedle device, according to the second embodiment, and here the fluid injector using the multi-microneedle device is disposed at a first protrusion position in the outer cylinder of the operational instrument by the selective transfer mechanism.
Figure 3C:
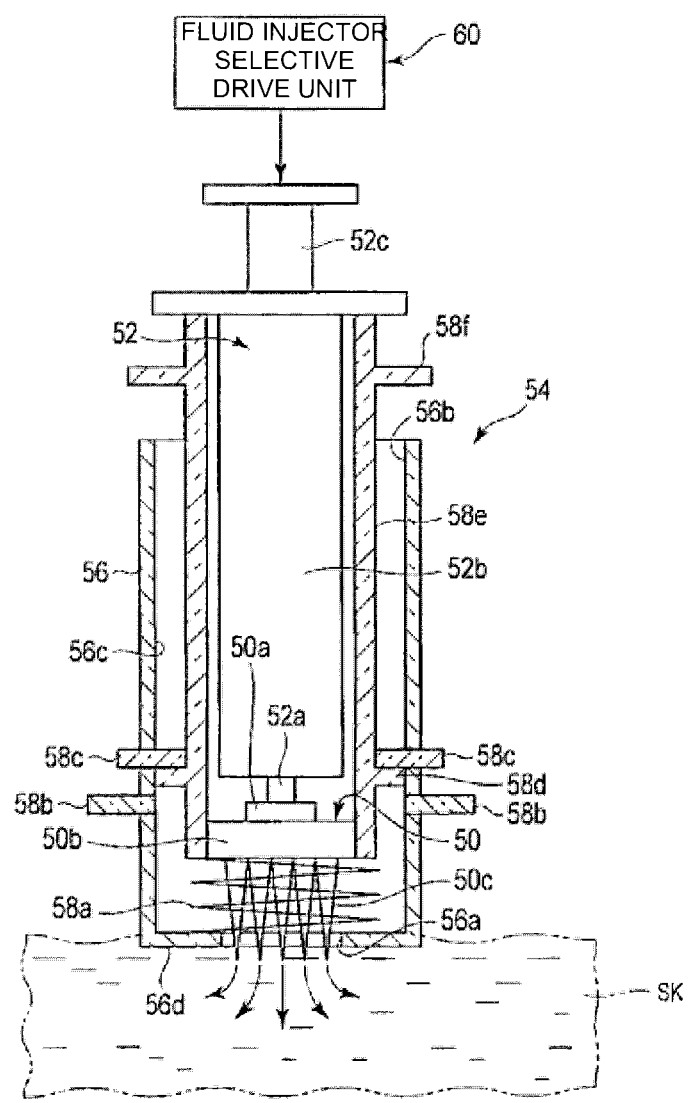
FIG. 3C is a schematic longitudinal sectional view of the operational instrument, for a fluid injector using a multi-microneedle device, according to the second embodiment, and here the fluid injector using the multi-microneedle device is disposed at a second protrusion position in the outer cylinder of the operational instrument by the selective transfer mechanism.

With reference to FIG. 3A to FIG. 3C, next is schematically described a structure of an operational instrument 54 for a fluid injector 52 using a multi-microneedle device, according to a second embodiment.

The fluid injector 52 using the multi-microneedle device 50 manipulated by the operational instrument 54 according to the second embodiment is studied to be used as, for example, a syringe in a medical field.

The fluid injector 52 has a fluid holding cylinder 52b (a syringe barrel in a syringe). The fluid holding cylinder 52b has a long and thin fluid holding space, a fluid outflow port 52a, and a fluid holding space inlet. The fluid holding space is capable of holding given fluid (for example, medicinal solution in a medical field). The fluid outflow port 52a is disposed at one end in longitudinal directions of the fluid holding space, and the fluid of the fluid holding space outflows from the fluid outflow port 52a. The fluid holding space inlet is disposed at the other one end in the longitudinal directions of the fluid holding space. The fluid injector 52 further has a piston member 52c set in the fluid holding space of the fluid holding cylinder 52b from the fluid holding space inlet such as to slide along the longitudinal axis.

It is considered that the multi-microneedle device 50 in a medical field is attached to an outflow port of a syringe barrel of a conventional syringe in place of one syringe needle well known in the medical field, and used for intradermal injection.

The multi-microneedle device 50 includes a main body 50b having an outflow port attachment port 50a detachably attached to the fluid outflow port 52a of the fluid (medicinal solution in a medical field) of the fluid holding cylinder 52b (syringe barrel in a syringe) of the fluid injector 52. The main body 50b forms a fluid holding space for temporarily holding fluid which has been subjected to pressure of a piston member 52c of the fluid injector 52 to be outflowed from the fluid outflow port 52a to the outflow port attachment port 50a. The multi-microneedle device 50 has a plurality of microneedles 50c disposed on a plane positioned on the opposite side to the outflow port attachment port 50a across the fluid holding space.

The multi-microneedle device 10 can be prepared by, for example, applying etching using a publicly known photolithography method on a silicon substrate. Moreover, by electroforming with the silicon multi-microneedle device as an original plate, a copy plate having a reversal shape is prepared. Thereby, a resin multi-microneedle device can also be prepared from the copy plate.

Regarding the multi-microneedle device, at least the plurality of microneedles 50c are preferred to be made of biocompatible materials, and whole of the multi-microneedle device is further preferred to be made of biocompatible materials. The biocompatible materials include a metal including, for example, stainless steel, titanium, manganese or the like, a resin including, for example, medical silicone, polylactic acid, polyglycolic acid, polycarbonate or the like, or an organic material such as silicon.

The above described biocompatible materials can be shaped into at least the plurality of the microneedle 50c of the multi-microneedle device or the whole of the multi-microneedle device by a publicly known forming technique such as injection forming, imprint, hot embossing, or casting.

The microneedles have respective fine fluid injection passages extending between base ends on the above plane and head ends away from the above plane. Lengths between the above respective base ends and the above respective head ends of the microneedles 50c, that is, respective heights of the microneedles 50c are set within a range of thicknesses of skin tissues of a living thing (for example, all human-beings) having the skin tissue as a use target, preferably within a range of thicknesses of the skin tissues having no nerves. Specifically, the height of the microneedle 50c is preferred to be set within a range of 100-2000 µm.

The microneedles have respective fine fluid injection passages extending between base ends on the above plane and head ends away from the above plane. Lengths between the above respective base ends and the above respective head ends of the microneedles 50c, that is, respective heights of the microneedles 50c are set within a range of thicknesses of skin tissues of a living thing (for example, all human-beings) having the skin tissue as a use target, preferably within a range of thicknesses of the skin tissues having no nerves. Specifically, the height of the microneedle 50c is preferred to be set within a range of 100-2000 µm.

Each whole shape of the microneedles 50c may be a cone shape including a circular cone or a pyramid, or, a column or a prism having a circular conic or a pyramid tip. Formation of the respective fine fluid outflow passages of the microneedles 50c can be carried out by a publicly known fine hole making process using, for example, a micro drill, a laser light, or the like.

The microneedles 50c on the above plane of the main body 10b can be arranged in a lattice pattern, in a concentric pattern, at random or the like, depending on purposes of use.

The operational instrument 54 according to the second embodiment has an outer cylinder 56. The outer cylinder 16 has a one opening end 56a, the other opening end 56b, and a fluid injector housing space 56c extending between the one opening end 56a and the other opening end 56b. The fluid injector housing space 56c holds the fluid injector 52 using the multi-microneedle device 50 such that the fluid injector 52 can move along the longitudinal axis of the fluid injector 52.

The operational instrument 54 according to the second embodiment is provided in the outer cylinder 56, and further has a selective transfer mechanism 58 that serially move the fluid injector 52 between an initial position, a first protrusion position and a second protrusion portion in the fluid injector housing space 56c of the outer cylinder 56.

The selective transfer mechanism 58 of the operational instrument 54 according to the second embodiment is configured to return the fluid injector 52 to the initial position after at the second position in the fluid injector housing space 56c of the outer cylinder 56.

In the fluid injector 52 at the initial position, the plurality of microneedles 50c of the multi-microneedle device 50, as shown in FIG. 3A, is drawn from the one opening end 56a of the outer cylinder 56 into the fluid injector housing space 56c.

In the fluid injector 52 at the first position, the plurality of microneedles 50c of the multi-microneedle device 50 are protruded by a first distance away from the one opening end 56a of the outer cylinder 56 to the external space, as shown in FIG. 3B.

In the fluid injector 52 at the second position, the plurality of microneedles 50c of the multi-microneedle device 50 are protruded by a second distance away from the one opening end 56a of the outer cylinder 56 to the external space, as shown in FIG. 3C. The second distance is shorter the aforementioned first distance.

In the operational instrument 54 according to the second embodiment, fluid flows out from the fluid injector 52 at the second protrusion position through the plurality of microneedles 50c of the multi-microneedle device.

In the second embodiment, the one opening end 56a of the outer cylinder 56 is an opening formed at the center portion of an end wall formed at the end of the outer cylinder 56. The opening has a predetermined diameter. The outer surface of the end wall of the outer cylinder 56 serves as a skin contact surface 56d.

The selective transfer mechanism 58 of the operational instrument 54 according to the second embodiment has a forcing unit 58a. The forcing unit 58a interposes in the fluid injector housing space 56c of the outer cylinder 56 between the main body 50b of the multi-microneedle device 50 and the inner surface of the aforementioned end wall of the outer cylinder 56, and forces the fluid injector 52 toward the aforementioned initial position shown in FIG. 3A.

In this embodiment, the forcing unit 58a is provided with a compression coil spring. Alternatively, for example, the forcing unit 58a can be an elastic material which is pressed to accumulate a repulsion force, such as a plate spring or a rubber.

The selective transfer mechanism 58 of the operational instrument 54 according to the second embodiment has a first stopper 58b. The first stopper 58b is provided at a first position, a predetermined distance away from the one opening end 56a of the aforementioned end wall inward, in the outer periphery wall of the outer cylinder 56, and is capable of appearing in the fluid injector housing space 56c selectively. The first stopper 58b is provided at the first position of the outer periphery wall of the outer cylinder 56 such that it can selectively appear in the fluid injector housing space 56c, for example, by a publicly known slide mechanism or a publicly known rotation mechanism.

The selective transfer mechanism 58 of the operational instrument 54 according to the second embodiment has a second stopper 58c. The second stopper 58c is provided at a second position, which is separated from the one opening end 56a of the aforementioned end wall and a predetermined distance away from the first position inward, in the outer periphery wall of the outer cylinder 56, and is capable of appearing in the fluid injector housing space 56c selectively. The second stopper 58c is provided at the second position of the outer periphery wall of the outer cylinder 56 such that it can selectively be disposed in the fluid injector housing space 56c or withdrawn, for example, by a publicly known slide mechanism or a publicly known rotation mechanism.

The selective transfer mechanism 58 of the operational instrument 54 according to the second embodiment further has an engagement portion 58d at the outer periphery wall of the fluid injector 52. The engagement portion 58d projects toward the outer periphery wall of the outer cylinder 56.

Further specifically, the selective transfer mechanism 58 has a cylindrical intermediate member 58e. The intermediate member 58e has an one opening end and the other opening end, and is disposed between the outer periphery wall of the outer cylinder 56 and the outer periphery wall of the fluid holding cylinder 52b (syringe barrel in a syringe) of the fluid injector 52 with the multi-microneedle device 50. The outer periphery surface of the multi-microneedle device 50 of the fluid injector 52 is fixed to the one opening end of the intermediate member 58e. The fluid injector 52 connected to the multi-microneedle device 50 is housed in the columnar space extending between the one end and the other opening end of the intermediate member 58e. The intermediate member 58e with the fluid injector accompanied the multi-microneedle device 50 is movable in the fluid injector housing space 56b of the outer cylinder 56 relative to the longitudinal axis of the outer cylinder 56, and the engagement portion 58d is formed at the outer periphery wall of the intermediate member 58e.

The multi-microneedle device 50 and the intermediate member 58e may be formed separately from each other, thereafter the multi-microneedle device 50 may be fixed to the intermediate member 58e by a publicly known fixing structure including, for example, an adhesive agent or snap-engagement. Alternatively, the multi-microneedle device 50 and the intermediate member 58e may be formed integrally at the same time.

The intermediate member 58e and the engagement portion 58d may be formed separately from each other, followed by fixing to the engagement portion 58d by a publicly known fixing structure including, for example, an adhesive agent or snap-engagement. Alternatively, the intermediate member 58e and the engagement portion 58d may be formed integrally at the same time.

That is, the engagement portion 58d of in this embodiment projects through the intermediate member 58e and the multi-microneedle device 50 from the outer periphery wall of the fluid injector 52 toward the outer periphery wall of the outer cylinder 56.

As shown in FIG. 3A, the fluid injector 52 connected to the multi-microneedle device 50 is disposed with the intermediate member 58e at the aforementioned initial position owing to the force of the forcing unit 58a, while the first stopper 58b and the second stopper 58c are disposed at a position where there are drawn from the outer cylinder 56 of the outer cylinder 56. At this position, the engagement portion 58d of the fluid injector 52 is positioned at the inside of the first stopper 58b and the second stopper 58c of the outer periphery wall of the outer cylinder 56 relative to the one opening end 56a of the outer cylinder 56.

The other end having the other opening end in the outer periphery wall of the intermediate member 58e protrudes from the other opening end 56b of the outer cylinder 56 to the external space, while the fluid injector 52 is disposed at the aforementioned initial position shown in FIG. 3A. An intermediate member operation projection 58f is formed at the other end of the outer periphery wall of the intermediate member 58e. The intermediate member operation protrusion 58f serves an auxiliary for the user to move the intermediate member 58e relatively to the outer cylinder 56 along the longitudinal axis of the outer cylinder 56 in the fluid injector housing space 56b of the outer cylinder 56.

The piston member 52c and the other end of the fluid holding cylinder 52b (syringe barrel in a syringe) of the fluid injector 52 connected to the multi-microneedle device 50 protrude from the other opening end of the intermediate member 58e.

In this embodiment, it is preferred that each of the outer cylinder 56, the intermediate member 58e and the fluid holding cylinder 52b (syringe barrel in a syringe) of the fluid injector 52 is made from transparent materials so that the amount of the fluid (medicinal solution in a medical field) held in the fluid holding cylinder 52b can be observed from the outside. In each of the outer cylinder 56 and the intermediate member 58e, only a portion corresponding to the fluid injector 52 and the fluid holding cylinder 52b, in the respective outer periphery wall thereof may be made from the transparent materials.

With reference to FIG. 3A to FIG. 3C, next is described a procedure of injecting the fluid (for example, a medicinal solution) held in the fluid injector 52 to skin tissue at a desired site where skin of a living thing (in this embodiment, for example, a human being) is exposed, operating the fluid injector 52 using the multi-microneedle device 50 with the operational instrument 54 according to the aforementioned second embodiment.

At first, the user of the operational instrument 54 according to the aforementioned second embodiment attaches the fluid outflow port 52a of the fluid holding cylinder 52b of the fluid injector 52 to the outflow port attachment port 50a of the multi-microneedle device 50, while the first stopper 58b and the second stopper 58c of the selective transfer mechanism 58 is disposed at the drawn position as shown in FIG. 3A and the intermediate 58e having the multi-microneedle device 50 is disposed at the initial position, as shown in FIG. 3A, owing to the force of the forcing unit 58a.

At this time, the plurality of microneedles 50c of the multi-microneedle device 50 disposed at the initial position as described above are drawn from the one opening end 56a of the outer cylinder 56 inside the fluid injector housing space 56b.

Further, the fluid holding body 52b of the fluid injector 52 has already been filled with the fluid (for example, a medicinal solution) for injecting to the skin tissue of the living thing (for example, a human being). By pushing the piston member 52c slightly, the fluid held in the fluid holding cylinder 52b is made flow into the fluid holding space of the main body 50b of the multi-microneedle device 50 and the fine fluid injection passages of the plurality of microneedles 10c of the multi-microneedle device 50, thereby filling these with the aforementioned fluid.

After that, the user holds the outer periphery surface of the outer cylinder 56, avoiding the contact with the first stopper 58b and the second stopper 58c of the selective transfer mechanism 58 disposed at the aforementioned drawn position. Subsequently, the user presses, to the desired site where the skin SK of the living thing (for example, a human being) is exposed, the skin contact surface 56d on the outer surface of the end surface of the end wall at the one end of the outer cylinder 56.

At this time, the desired site where the skin SK is exposed is pressed inside the skin SK by the skin contact surface 56d of the aforementioned end wall of the outer cylinder 56.

Next, the intermediate member operation projection 58f of the intermediate member 58e is pushed to move the intermediate member 58e against the force of the forcing unit 58a toward the end wall of the outer cylinder 56 until the engagement portion 58d of the intermediate 58e passes the second stopper 58c and the first stopper 58b at the withdrawn positions.

Thereafter, the second stopper 58c and the first stopper 58b are moved to protrusion positions as shown in FIG. 3B, followed by releasing the push to the intermediate member operation projection 58f of the intermediate member 58e. As a result, although the intermediate member 58e to which the multi-microneedle device 50 is fixed tends to return to the initial position in FIG. 3A because of the force of the forcing unit 58a, the engagement portion 58d of the intermediate member 58e engages the first stopper 58b at the protrusion position as shown in FIG. 3B. This allows the intermediate member 58e fixing the multi-microneedle device 50 to be held at the first protrusion position against the force of the forcing unit 58a.

Thus, the plurality of microneedles 50c of the multi-microneedle device 50 moved from the initial position shown in FIG. 3A to the first protrusion position shown in FIG. 3B protrude by the first distance from the one opening end 56a to the outside. At this time, the plurality of microneedles 50c reliably pierce the region surrounded by the one opening end 56a of the end wall of the outer cylinder 56 at the aforementioned desired site of the exposed skin SK pressed by the skin contact surface 56d of the end wall of the outer cylinder 56, as shown in FIG. 3B.

At this time, the elasticity of the skin tissue of the above region at the aforementioned desired site of the exposed skin SK is reduced in some degree.

Subsequently, the first stopper 58b of the selective transfer mechanism 18 is moved to the withdrawn position, as shown in FIG. 3C. As a result, although the intermediate member 58e fixing the multi-microneedle device 50 tends to return to the initial position in FIG. 3A because of the force of the forcing unit 58a, the engagement portion 58d of the intermediate member 58e engages the second stopper 58c at the protrusion position as shown in FIG. 3C. This allows the intermediate member 58e fixing the multi-microneedle device 50 to be held at the second protrusion position against the force of the forcing unit 58a.

Thus, the plurality of microneedles 50c of the multi-microneedle device 50 moved from the first protrusion position shown in FIG. 3B to the second protrusion position shown in FIG. 3C protrude by the second distance from the one opening end 56a. The second distance is shorter than the first distance.

The plurality of microneedles 50c of the multi-microneedle device 50 moved to the second protrusion position weakens the pressing force to the region surrounded by the one opening end 16a of the outer cylinder 56 at the aforementioned desired site of the exposed skin SK. This causes the elasticity to recover, thereby the above region follows the plurality of microneedles 50c. As a result, piercing the above region by the plurality of microneedles 50c is kept, as shown in FIG. 3C.

The user presses the piston member 52c of the fluid injector 52, while the multi-microneedle device 50 is disposed at the second protrusion position shown in FIG. 3C as described above. As a result, the fluid filling the fluid holding cylinder 52b of the fluid injector 52, the fluid holding space of the main body 50b of the multi-microneedle device 50 and the fine fluid injection passages of many microneedles 50c as described above can easily and quickly be injected, through the fine fluid injection passages of many microneedles 50c of the multi-microneedle device 50, to the inside of the skin tissue of the aforementioned region where the elasticity is recovered at the aforementioned desired site of the exposed skin SK, depending on the distance of the press, without leaking outside the skin SK as shown by a plurality of arrows in FIG. 3C.

In the case where the outer cylinder 56 of the operational instrument 54, the intermediate member 58e and the fluid holding cylinder 52b of the fluid injector 52 are made from the transparent materials as described above, the user can easily confirm the injection amount of the aforementioned fluid by observing it through the outer cylinder 56 of the operational instrument 54, the intermediate member 58e and the fluid holding cylinder 52b of the fluid injector 52.

After finishing the injection from the fluid injector 52 through many microneedles 50c of the multi-microneedle device 50 to the inside of the skin tissue of the aforementioned region at the aforementioned desired site of exposed skin SK, the operational instrument 54 is separated from the aforementioned desired site of the exposed skin SK, and the multi-microneedle device 50 is pulled away from the skin tissue of the aforementioned region at the aforementioned site of the exposed skin SK at the same time.

Before or after separating the manipulation 54 the operational instrument 54 from the aforementioned desired site of the exposed skin SK, the second stopper 58c is moved to the withdrawn position. As a result, the intermediate member 58e to which the multi-microneedle device 50 is fixed is subjected to the force of the forcing unit 58a to return to the initial position in FIG. 3A.

In the aforementioned embodiment, the user presses the piston member 52c exposed outside the fluid injector 52, while many microneedles 50c of the multi-microneedle device 50 are disposed at the second protrusion position as shown in FIG. 3C. Alternatively, pressing the piston member 52c during this can be performed by a fluid injector selective drive unit 60, as shown in FIG. 3A.

Such a fluid injector selective drive unit 60 can be fixed detachably to a portion opposite to the multi-microneedle device 50 in the outer periphery surface of the intermediate member 58e, and is configured to selectively press the external exposed end of the piston member 52c as described above. This configuration can include a drive member not shown in the drawings, a force generation source not shown in the drawings, and a switching mechanism not shown in the drawings. The drive member contacts the external exposed end of the piston member 52c. The force generation source gives the drive member force toward the external exposed end of the piston member 52c. The switching mechanism makes the force generation mechanism not shown in the drawings generate the force selectively.

Further specifically, for example, the force generation source not shown in the drawings can be selected from a compression spring, an extension spring, an elastic material, and a supply source of compressed gas including compressed air. The switching mechanism can be a publicly known latch mechanism, trigger mechanism or push clasp mechanism keeping stopping the movement against the force generated from the force generation source, or a manual-powered or electromagnetically-driven ON-OFF valve that can selectively supply the drive member not shown in the drawings the compressed gas including compressed air from a compressed gas supply source.

First Modification of Second Embodiment

Figure 4:
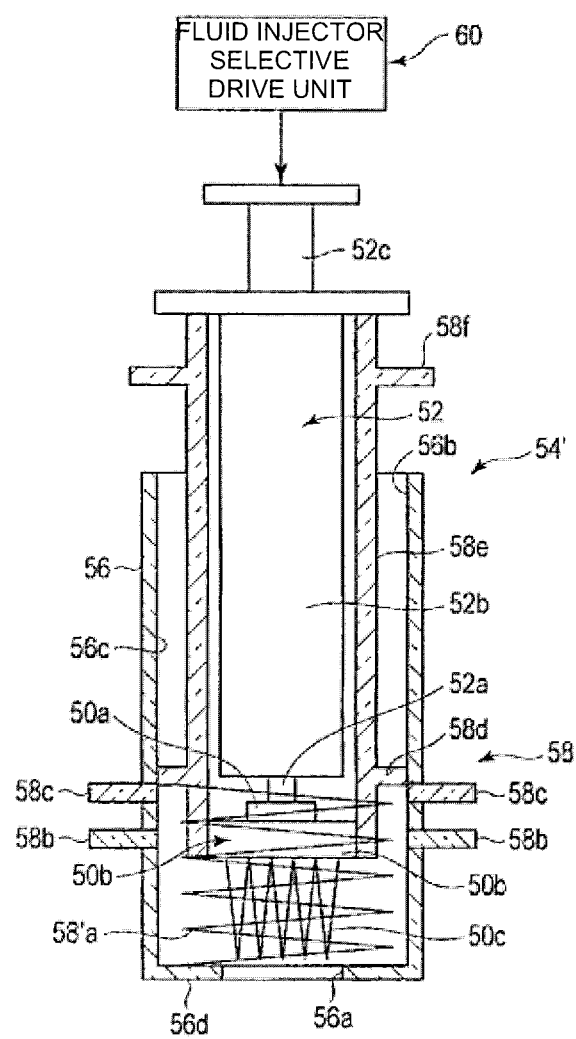
FIG. 4 is a schematic longitudinal sectional view of a first modification of the operational instrument, for a fluid injector using a multi-microneedle device, according to the second embodiment, and here the fluid injector using the multi-microneedle device is disposed at an initial position in an outer cylinder of the operational instrument by a selective transfer mechanism.

With reference to FIG. 4, hereinafter is described a first modification of the operational instrument 54 according to the second embodiment shown in FIG. 3A to FIG. 3C.

Most part of the configuration of the operational instrument 54' of the first modification is the same as most part of the configuration of the operational instrument 54 according to the second embodiment shown in FIG. 3A to FIG. 3C. Accordingly, in the operational instrument 54' of the first modification shown in FIG. 4, the same reference signs are used for the same components as the components of the operational instrument 54 according to the second embodiment shown in FIG. 3A to FIG. 3C, and detailed descriptions for these components are omitted.

The difference of the operational instrument 54' of the first modification from the operational instrument 54 according to the second embodiment is a placement of a forcing unit 58'a inside the fluid injector housing space 56c of the outer cylinder 56. In the first modification, the forcing unit 58'a is interposed between the engagement portion 58d of the intermediate member 58e fixed to the main body 50b of the multi-microneedle device 50 in the fluid injector housing space 56 of the outer cylinder 56 and the inner surface of the aforementioned end wall of the outer cylinder 56.

In FIG. 4, there is shown a case where the forcing unit 58'a is a compression coil spring. In this case, the end, near the engagement portion 58d of the intermediate member 58e, of the compression coil spring is wound around the end, near the engagement portion 58d, in the outer periphery of the intermediate member 58e, and both ends of the compression coil spring contact the engagement portion 58d of the intermediate member 58e and the inner surface of the aforementioned end wall of the outer cylinder 56.

First Modification of Second Embodiment

Figure 5:
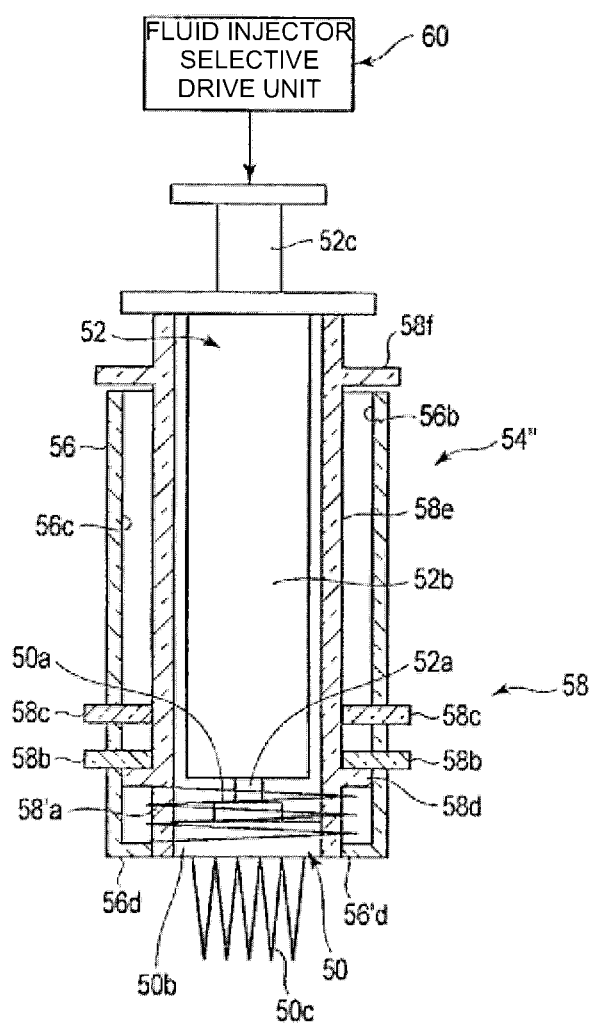
FIG. 5 is a schematic longitudinal sectional view of a second modification of the operational instrument, for a fluid injector using a multi-microneedle device, according to the second embodiment, and here the fluid injector using the multi-microneedle device is disposed at a first protrusion position in an outer cylinder of the operational instrument by a selective transfer mechanism.

With reference to FIG. 5, hereinafter is described a second modification of the operational instrument 54 according to the second embodiment shown in FIG. 3A to FIG. 3C.

Most part of the configuration of the operational instrument 54" of the second modification is the same as most part of the configuration of the operational instrument 54 according to the second embodiment shown in FIG. 3A to FIG. 3C. Accordingly, in the operational instrument 54" of the second modification shown in FIG. 5, the same reference signs are used for the same components as the components of the operational instrument 54 according to the second embodiment shown in FIG. 3A to FIG. 3C, and detailed descriptions for these components are omitted.

The differences of the operational instrument 54" of the second modification from the operational instrument 54 according to the second embodiment are the placement of the forcing unit 58'a in the fluid injector housing space 56c of the outer cylinder 56 and the size of an one opening end 56'a of the aforementioned end wall of the outer cylinder 56.

The forcing unit 58'a of the second modification is the same as the forcing unit 58'a of the operational instrument 54' of the first modification shown in FIG. 4. That is, this forcing unit 58'a is interposed between the engagement portion 58d of the intermediate member 58e fixed to the main body 50b of the multi-microneedle device 50 in the fluid injector housing space 56 of the outer cylinder 56 and the inner surface of the aforementioned end wall of the outer cylinder 56.

In FIG. 5, there is shown a case where the forcing unit 58'a is a compression coil spring. In this case, the end, near the engagement portion 58d of the intermediate member 58e, of the compression coil spring is wound around the end, near the engagement portion 58d, in the outer periphery of the intermediate member 58e, and both ends of the compression coil spring contact the engagement portion 58d of the intermediate member 58e and the inner surface of the aforementioned end wall of the outer cylinder 56.

The size, in radial direction of the outer cylinder 56, of the one opening end 56'a in the aforementioned end wall of the outer cylinder 56 of the operational instrument 54" of the second modification is set slightly larger than the size, in radial direction of the outer cylinder 56, of the main body 50b of the multi-microneedle device 50.

Further, the distance of the first stopper 58b in the outer periphery wall of the outer cylinder 56 from the skin contact surface 56d of the aforementioned end wall of the outer cylinder 56 is set shorter than the distance of the first stopper 58b in the outer periphery wall of the outer cylinder 56 from the skin contact surface 56d of the aforementioned end wall of the outer cylinder 56 in the second embodiment described above referring to FIG. 3A to FIG. 3C. As a result, in the second modification, when the engagement portion 58d of the intermediate member 58e fixing the multi-microneedle device 50 engages the first stopper 58b disposed at the protrusion position in the outer periphery wall of the outer cylinder 56 and holds many multi-microneedles 50c of the multi-microneedle device 50 at the first protrusion position against the force of the forcing unit 58'a, the main body 50b of the multi-microneedle device 50 enters in the one opening end 56'a of the aforementioned end wall of the outer cylinder 56 of the operational instrument 54", and the outer end surface of the main body 50b and the skin contact surface 56d of the aforementioned end wall of the outer cylinder 56 of the operational instrument 54" are disposed on the substantially same plane.

When intradermal injection is carried out by the syringe using the multi-microneedle device, a fluid (for example, a medicinal solution) to be used for intradermal injection is preliminarily fed through the fluid outflow port of the syringe barrel into the syringe barrel. Subsequently, the outflow port attachment port of the multi-microneedle device is detachably attached to the fluid outflow port of the syringe barrel. Thereafter, the piston member of the syringe is slightly pressed to push the air from the fluid holding space of the multi-microneedle device and the respective fine fluid injection passages of the plurality of microneedles with the fluid from the syringe barrel, thereby filling the fluid hold space of the multi-microneedle device and the respective fine fluid injection passages of the plurality of microneedles with the fluid.

Next, a desired site where skin of a living thing (for example, a human being) is exposed is pushed by the skin contact surface of the main body of the multi-microneedle device. This pushing allows the plurality of microneedles on the skin contact surface to pierce the skin tissue at the desired site of the exposed skin of the living thing (for example, a human being). Subsequently, on pushing the piston member of the syringe, the fluid from the syringe is injected, through the fluid fold space of the multi-microneedle device and the respective fine fluid injection passages of the plurality of microneedles, into the skin tissue at the desired site of exposed skin of the living thing (for example, a human being).

When intradermal injection is carried out by the syringe using the multi-microneedle device, the piston member of the syringe is pressed, pushing the desired site of the exposed skin of the living thing (for example, a human being) by the skin contact surface of the main body of the multi-microneedle device. In this case, because a force pressing the piston member of the syringe in addition to the pressure from the skin contact surface of the main body of the multi-microneedle device is loaded on the desired site of the exposed skin, the skin tissue at the desired site of the exposed skin is compressed and the elasticity thereof is reduced by some degree. As a result, when intradermal injection is carried out by the syringe using the multi-microneedle device, all amount of the fluid (for example, a medicinal solution) from the plurality of microneedles cannot be injected into the skin tissue at the desired site, which causes the fluid to leak to a surface of the skin at the desired site. Also, it takes a comparatively long time to inject the whole desired amount of the fluid into the skin tissue at the desired site.

One aspect of the present invention is to provide an operational instrument for a fluid injector using a multi-microneedle device, by which anyone can readily and reliably inject the whole desired amount of a fluid into skin tissue at a desired site in a brief period of time in instances of intradermal injection to the skin tissue at the desired site with a fluid injector using a multi-microneedle device, such as, for example, a syringe.

An operational instrument for a fluid injector using a multi-microneedle device according to an aspect of the present invention has:

an outer cylinder having one opening end, another opening end, and a fluid injector housing space extending between the one opening end and the other opening end, the fluid injector housing space holding the fluid injector using the multi-microneedle device movable along a longitudinal axis of the fluid injector; and a selective transfer mechanism provided at the outer cylinder and moving the fluid injector between an initial position, a first protrusion position and a second protrusion position in the fluid injector holding space of the outer cylinder sequentially, a plurality of microneedles of the multi-microneedle device being retracted from the one opening end of the outer cylinder inside the fluid injector housing space at the initial position, the plurality of microneedles of the multi-microneedle device being externally protruded out to a first distance from the one opening end of the outer cylinder at the first protrusion position, the plurality of microneedles of the multi-microneedle device being externally protruded out to a second distance from the one opening end of the outer cylinder at the second protrusion position, the second distance being shorter than the first distance, wherein, at the second protrusion position, fluid is discharged from the fluid injector through the plurality of microneedles of the multi-microneedle device.

An operational instrument for a fluid injector using a multi-microneedle device according to an aspect of the present invention is characterized by having these configurations:

In the fluid injector housing space extending between the one opening end and the other opening end of the outer cylinder, the fluid injector using the multi-microneedle device which is held movable along the longitudinal axis of the fluid injector is moved, by the selective transfer mechanism provided at the outer cylinder, between the initial position, the first protrusion position and the second protrusion position in the fluid injector holding space of the outer cylinder sequentially. The plurality of microneedles of the multi-microneedle device is retracted from the one opening end of the outer cylinder inside the fluid injector housing space at the initial position. The plurality of microneedles of the multi-microneedle device is externally protruded out to the first distance from the one opening end of the outer cylinder at the first protrusion position. The plurality of microneedles of the multi-microneedle device is externally protruded out to the second distance from the one opening end of the outer cylinder at the second protrusion position, the second distance being shorter than the first distance. At the second protrusion position, fluid is discharged from the fluid injector through the plurality of microneedles of the multi-microneedle device.

At the first protrusion position, the plurality of microneedles of the multi-microneedle device can pierce the skin tissue at the above-described desired site sufficiently. The skin contact surface of the main body of the multi-microneedle device can press the desired site of exposed skin of the living thing sufficiently.

At this time, the force of the plurality of microneedles of the multi-microneedle device pressing the desired site of exposed skin of the living thing reduces the elasticity of the desired site of exposed skin. This trend is further increased as the skin contact surface of the main body of the multi-microneedle device presses the desired site of exposed skin of the living thing sufficiently as described above.

Next, at the second protrusion position, the force of the plurality of microneedles of the multi-microneedle device pressing the desired site of exposed skin of the living thing can be loosened. That is, the elasticity of the desired site of exposed skin recovers. This trend is strengthened when the skin contact surface of the main body of the multi-microneedle device contacts the desired site of exposed skin of the living thing as described above.

At such a second protrusion position, the fluid is discharged from the fluid injector through the plurality of microneedles of the multi-microneedle device. This enable the fluid discharged from the plurality of microneedles to be injected into the skin tissue at the desired site of exposed skin of the living thing quickly.

Anyone can reliably perform the movement of the fluid injector using the multi-microneedle device from the initial position to the first protrusion position and from the first protrusion position to the second protrusion position relative to the outer cylinder, by operating the selective transfer mechanism provided at the outer cylinder.

Accordingly, by using the operational instrument for a fluid injector using a multi-microneedle device, characterized by having these configurations, anyone can readily and reliably inject the whole desired amount of a fluid into skin tissue at a desired site in a brief period of time in instances of intradermal injection to the skin tissue at the desired site with a fluid injector using a multi-microneedle device, such as, for example, a syringe.

DESCRIPTION OF REFERENCE NUMERALS

10 . . . multi-microneedle device, 10a . . . outflow port attachment port, 10b . . . main body, 10d . . . skin contact surface, 12 . . . fluid injector, 12a . . . fluid outflow port, 12b . . . fluid holding cylinder, 12c . . . piston member, 12d . . . flange, 14 . . . operational instrument, 16 . . . outer cylinder, 16a . . . one opening end, 16b . . . the other opening end, 16c . . . fluid injector housing space, 16d . . . part, 16e . . . parting line, 18 . . . selective transfer mechanism, 18a . . . operational member, 18b . . . following mechanism, 18c . . . arm, 18d . . . hook portion, 18e . . . protrusion (following mechanism), 20 . . . forcing unit (compression coil spring), 22 . . . first outer cylinder part, 22a . . . gap, 22b . . . operational member disposed opening, 24 . . . second outer cylinder, 24a . . . one end, 24b . . . the other end, 24c . . . elongate hole, 25 . . . lid, 26 . . . fluid injector holding body, 26a . . . protrusion, 26b . . . fluid injector hold trench, 26c . . . piston member housing trench, 28 . . . piston member pressing rod, 28a . . . fine length regulation mechanism, 28b . . . fine length regulation dial, 28c . . . sub forcing means (compression coil spring), RC . . . rotating cam (following mechanism), DM . . . rotating cam rotation drive member (following mechanism), 30 . . . fluid injector selective drive unit:

50 . . . multi-microneedle device, 50a . . . outflow port attachment port, 50b . . . main body, 50c . . . microneedle, 52 . . . fluid injector, 52a . . . fluid outflow port, 52b . . . fluid holding cylinder, 52c . . . piston member, 54 . . . operational instrument, 56 . . . outer cylinder, 56a . . . one opening end, 56b . . . the other opening end, 56c . . . fluid injector housing space, 56d . . . skin contact surface, 58 . . . selective transfer mechanism, 58a . . . forcing unit, 58b . . . first stopper, 58c . . . second stopper, 58d . . . engagement portion, 58e . . . intermediate member, 58f . . . intermediate member operation projection, 60 . . . fluid injector selective drive unit:

54' . . . operational instrument, 58'a . . . forcing unit;

54" . . . operational instrument, 56'a . . . one opening end.

Obviously, numerous modifications and variations of the present invention are possible in light of the above teachings. It is therefore to be understood that within the scope of the appended claims, the invention may be practiced otherwise than as specifically described herein.

The invention claimed is:

1. An operation tool, comprising:

an outer cylinder having a first open end, a second open end, and a cylinder body extending from the first open end to the second open end, the cylinder body being formed such that a fluid injector having a multi-microneedle device with a plurality of microneedles is movable in the cylinder body along a longitudinal axis of the fluid injector and has the microneedles extended out of or retracted from the first open end of the outer cylinder; and a selective transfer mechanism provided on the outer cylinder and comprising a rotating cam and a rotating cam rotation drive member configured to control a rotational movement of the rotating cam such that the rotating cam rotation drive member rotates the rotating cam to move the fluid injector from an initial position in the cylinder body of the outer cylinder to a first protrusion position and hold the fluid injector in the first protrusion position and rotates the rotating cam to move the fluid injector from the first protrusion position to a second protrusion position and hold the microneedles extended out of the outer cylinder from the first open end in the second protrusion position, wherein the selective transfer mechanism is configured such that, when the rotating cam holds the fluid injector in the initial position, the multi-microneedle device has the microneedles retracted from the first open end of the outer cylinder and positioned inside the cylinder body, when the rotating cam holds the fluid injector in the first protrusion position, the microneedles are protruded and positioned at a first distance from the first open end, and when the rotating cam holds the fluid injector in the second protrusion position to discharge fluid through the microneedles of the multi-microneedle device, the microneedles are protruded and positioned at a second distance from the first open end such that the second distance is shorter than the first distance, and the selective transfer mechanism is configured to return the fluid injector to the initial position by a further control of the rotational movement of the rotating cam after the fluid injector is held at the second protrusion position.

2. The operation tool according to claim 1, wherein the selective transfer mechanism is configured to move the fluid injector such that a skin contact surface of a main body of the multi-microneedle device is moved, and the selective transfer mechanism is configured such that, when the fluid injector is at the initial position, the skin contact surface and the microneedles are retracted from the first open end of the outer cylinder and positioned inside the cylinder body, when the fluid injector is at the first protrusion position, the skin contact surface and the microneedles are protruded out to the first distance from the first open end, and when the fluid injector is at the second protrusion position, the skin contact surface and the microneedles are protruded out to the second distance from the first open end.

3. The operation tool according to claim 2, wherein the selective transfer mechanism includes: an operation member provided movable relative to an outer periphery surface of the outer cylinder; and a follow mechanism configured to follow operation of the operation member and move the fluid injector from the initial position to the first protrusion position and then to the second protrusion position in the cylinder body, following the operation of the operation member.

4. The operation tool according to claim 3, wherein the operation member is extended in a longitudinal direction of the outer cylinder in the outer periphery surface of the outer cylinder, the operation member is rotatable with a first end portion fixed as a rotational center and movable between a protruded position and a drawn position such that the operation member at the protruded position has a second end portion protruded from the outer periphery surface of the outer cylinder, and that the operation member at the drawn position has the second end portion located closer to the outer periphery surface than the second end portion of the operation member at the protruded position, the selective transfer mechanism is configured such that when the fluid injector is at the initial position in the cylinder body, the operation member is at the protruded position, and the follow mechanism is configured such that when the operation member is moved from the protruded position to the drawn position, the fluid injector is moved from the initial position to the first protrusion position, and when the operational member is returned from the drawn position to the protrusion position, the follow mechanism moves the fluid injector from the first protrusion position to the second protrusion position and holds the fluid injector at the second protrusion position.

5. The operation tool according to claim 2, wherein the selective transfer mechanism has a spring configured to apply a force to the fluid injector toward the initial position in the cylinder body, and the selective transfer mechanism is configured such that the fluid injector is moved from the initial position to the first protrusion position against the force of the spring, moved from the first protrusion position to the second protrusion position by the force of the spring, and is held at the second protrusion position against the force of the spring.

6. The operation tool according to claim 1, wherein the selective transfer mechanism has a forcing unit configured to apply a force to the fluid injector toward the initial position in the cylinder body, and the selective transfer mechanism is configured such that the fluid injector is moved from the initial position to the first protrusion position against the force of the forcing unit, moved from the first protrusion position to the second protrusion position by the force of the forcing unit, and is held at the second protrusion position against the force of the forcing unit.

7. The operation tool according to claim 1, wherein the selective transfer mechanism includes: an operation member provided movable relative to an outer periphery surface of the outer cylinder; and a follow mechanism configured to follow operation of the operation member and move the fluid injector from the initial position to the first protrusion position and then to the second protrusion position in the cylinder body, following the operation of the operation member.

8. The operation tool according to claim 7, wherein the operation member is extended in a longitudinal direction of the outer cylinder in the outer periphery surface of the outer cylinder, the operation member is rotatable with a first end portion fixed as a rotational center and movable between a protruded position and a drawn position such that the operation member at the protruded position has a second end portion protruded from the outer periphery surface of the outer cylinder, and that the operation member at the drawn position has the second end portion located closer to the outer periphery surface than the second end portion of the operation member at the protruded position, the selective transfer mechanism is configured such that when the fluid injector is at the initial position in the cylinder body, the operation member is at the protruded position, and the follow mechanism is configured such that when the operation member is moved from the protruded position to the drawn position, the fluid injector is moved from the initial position to the first protrusion position, and when the operational member is returned from the drawn position to the protrusion position, the follow mechanism moves the fluid injector from the first protrusion position to the second protrusion position and holds the fluid injector at the second protrusion position.

9. The operation tool according to claim 1, wherein the selective transfer mechanism has a spring configured to apply a force to the fluid injector toward the initial position in the cylinder body, and the selective transfer mechanism is configured such that the fluid injector is moved from the initial position to the first protrusion position against the force of the spring, moved from the first protrusion position to the second protrusion position by the force of the spring, and is held at the second protrusion position against the force of the spring.

10. The operation tool according to claim 9, further comprising:
a fluid injector holding body configured to detachably hold the fluid injector; and
a piston member pressing rod penetrating through the rotating cam and the rotating cam rotation drive member and configured to engage with the fluid injector held by the fluid injector holding body,
wherein the fluid injector includes a cylinder that holds the fluid, and a piston member that discharges the fluid from the cylinder.

11. The operation tool according to claim 1, wherein the fluid injector is housed detachably relative to the cylinder body of the outer cylinder.

12. The operation tool according to claim 11, wherein an outer periphery wall of the outer cylinder has a detachable portion such that when the detachable portion is detached from the rest of the outer periphery wall, the fluid injector is attached to or detached from the cylinder body of the outer cylinder.

13. The operation tool according to claim 12, wherein the fluid injector includes a cylinder for holding the fluid and has a confirmation structure which allows confirmation of an amount of the fluid held in the cylinder from an outside, and the detachable portion of the outer periphery wall of the outer cylinder has a structure which allows observation of the confirmation structure when the detachable portion is attached to the rest of the outer periphery wall of the outer cylinder.

14. The operation tool according to claim 1, further comprising:
a fluid injector selective drive unit configured to selectively drive the fluid injector to discharge the fluid held in the fluid injector through the multi-microneedle device.

15. The operation tool according to claim 1, further comprising:
a fluid injector holding body configured to detachably hold the fluid injector and having a detachable portion made of a transparent material.

16. An operation tool, comprising:
an outer cylinder having a first open end, a second open end, and a cylinder body extending from the first open end to the second open end, the cylinder body being formed such that a fluid injector having a multi-microneedle device with a plurality of microneedles is movable in the cylinder body along a longitudinal axis of the fluid injector and has the microneedles extended out of or retracted from the first open end of the outer cylinder; and
a selective transfer mechanism provided on the outer cylinder and comprising a rotating cam and a rotating cam rotation drive member configured to control a rotational movement of the rotating cam such that the rotating cam rotation drive member rotates the rotating cam to move the fluid injector from an initial position in the cylinder body of the outer cylinder to a first protrusion position and hold the fluid injector in the first protrusion position and rotates the rotating cam to move the fluid injector from the first protrusion position to a second protrusion position and hold the microneedles extended out of the outer cylinder from the first open end in the second protrusion position,
wherein the selective transfer mechanism is configured such that, when the rotating cam holds the fluid injector in the initial position, the multi-microneedle device has the microneedles retracted from the first open end of the outer cylinder and positioned inside the cylinder body, when the rotating cam holds the fluid injector in the first protrusion position, the microneedles are protruded and positioned at a first distance from the first open end, and when the rotating cam holds the fluid injector in the second protrusion position to discharge fluid through the microneedles of the multi-microneedle device, the microneedles are protruded and positioned at a second distance from the first open end such that the second distance is shorter than the first distance, the selective transfer mechanism has a spring configured to apply a force to the fluid injector toward the initial position in the cylinder body, and the selective transfer mechanism is configured such that the fluid injector is moved from the initial position to the first protrusion position against the force of the spring, moved from the first protrusion position to the second protrusion position by the force of the spring, and is held at the second protrusion position against the force of the spring.

17. The operation tool according to claim 16, wherein the fluid injector is detachably housed in the cylinder body of the outer cylinder.

18. The operation tool according to claim 17, wherein an outer periphery wall of the outer cylinder has a detachable portion such that when the detachable portion is detached from the rest of the outer periphery wall, the fluid injector is attached to or detached from the cylinder body of the outer cylinder.

19. The operation tool according to claim 18, wherein the fluid injector includes a cylinder for holding the fluid and has a confirmation structure which allows confirmation of an amount of the fluid held in the cylinder from an outside, and the detachable portion of the outer periphery wall of the outer cylinder has a structure which allows observation of the confirmation structure when the detachable portion is attached to the rest of the outer periphery wall of the outer cylinder.

20. The operation tool according to claim 16, wherein the outer cylinder has a first outer cylinder part and a second outer cylinder part positioned in an internal space of the first outer cylinder part, and the forcing unit comprises a compression coil spring wound around the second outer cylinder part.

\* \* \* \* \*